US009243939B2

(12) United States Patent
Tanoura et al.

(10) Patent No.: US 9,243,939 B2
(45) Date of Patent: Jan. 26, 2016

(54) FLOW VOLUME MEASUREMENT DEVICE AND FLOW VELOCITY MEASUREMENT DEVICE

(75) Inventors: Masazumi Tanoura, Tokyo (JP); Kenji Muta, Tokyo (JP); Atsushi Takita, Tokyo (JP); Minoru Danno, Tokyo (JP); Shinichiro Asami, Tokyo (JP); Kageharu Moriyama, Tokyo (JP); Daishi Ueno, Tokyo (JP); Ichiro Awaya, Tokyo (JP); Tadashi Aoki, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 765 days.

(21) Appl. No.: 13/580,411

(22) PCT Filed: Nov. 22, 2010

(86) PCT No.: PCT/JP2010/070832
§ 371 (c)(1),
(2), (4) Date: Aug. 22, 2012

(87) PCT Pub. No.: WO2011/129029
PCT Pub. Date: Oct. 20, 2011

(65) Prior Publication Data
US 2012/0323502 A1 Dec. 20, 2012

(30) Foreign Application Priority Data

Apr. 13, 2010 (JP) .................................. 2010-092574

(51) Int. Cl.
*G01F 1/00* (2006.01)
*G01F 1/20* (2006.01)
(Continued)

(52) U.S. Cl.
CPC ........ *G01F 1/00* (2013.01); *G01F 1/203* (2013.01); *G01F 1/661* (2013.01); *G01P 13/0066* (2013.01); *G01N 21/359* (2013.01)

(58) Field of Classification Search
CPC .......... G01F 1/00; G01F 1/661; G01F 1/203; G01P 13/0066; G01N 21/359; G01N 21/21; G01J 3/433

USPC ............................................................. 702/47
See application file for complete search history.

(56) References Cited

U.S. PATENT DOCUMENTS 4,719,360 A * 1/1988 Kontani et al. ................ 250/574
4,966,462 A * 10/1990 Novick .......................... 356/437
(Continued)

FOREIGN PATENT DOCUMENTS

| CN | 1325020 | 12/2001 |
|---|---|---|
| EP | 2 239 545 | 10/2010 |

(Continued)

OTHER PUBLICATIONS

Korean Office Action mailed Oct. 21, 2013 in corresponding Korean Application No. 10-2012-7021948, with English translation.
(Continued)

*Primary Examiner* — John Breene
*Assistant Examiner* — Eyob Hagos
(74) *Attorney, Agent, or Firm* — Wnederoth, Lind & Ponack, L.L.P.

(57) ABSTRACT

A flow volume measurement device or a flow velocity measurement device include a measurement cell including a main pipe, an incident tube that is connected to the main pipe, an emission tube that is connected to the main pipe, and a first purge-fluid supply tube that is connected to the incident tube, a purge-fluid supply unit that supplies purge fluid into the first purge-fluid supply tube of the measurement cell, a light emitting unit that emits a laser beam to the measurement cell, a light receiving unit that receives the laser beam emitted from the light emitting unit and having passed through the measurement cell, and outputs a received amount of light as a light reception signal, a calculation unit that calculates a flow volume or a flow velocity of exhaust fluid flowing in the measurement cell, based on a light reception signal output from the light receiving unit.

21 Claims, 17 Drawing Sheets

(51) Int. Cl.
*G01F 1/66* (2006.01)
*G01P 13/00* (2006.01)
*G01N 21/359* (2014.01)

(56) References Cited

U.S. PATENT DOCUMENTS

| | | | |
|---|---|---|---|
| 5,271,675 A * | 12/1993 | Fagan et al. | 374/110 |
| 5,326,969 A | 7/1994 | Fagan et al. | |
| 5,488,224 A | 1/1996 | Fagan et al. | |
| 5,587,785 A * | 12/1996 | Kato et al. | 356/28.5 |
| 5,668,327 A * | 9/1997 | Amemori et al. | 73/861.77 |
| 5,920,018 A | 7/1999 | Wilkerson et al. | |
| 2002/0108437 A1 | 8/2002 | Koch | |
| 2004/0060365 A1* | 4/2004 | Crudge et al. | 73/861 |
| 2004/0233452 A1 | 11/2004 | Prelewitz | |
| 2005/0032014 A1* | 2/2005 | Doebbeling et al. | 431/350 |
| 2005/0126281 A1* | 6/2005 | Blakley et al. | 73/204.21 |
| 2007/0192047 A1* | 8/2007 | Foucault et al. | 702/47 |
| 2008/0088819 A1 | 4/2008 | Metzger et al. | |
| 2010/0139414 A1* | 6/2010 | Sanderson | 73/861.19 |

FOREIGN PATENT DOCUMENTS

| | | |
|---|---|---|
| EP | 2 249 129 | 11/2010 |
| JP | 3-113127 | 11/1991 |
| JP | 06-174510 | 6/1994 |
| JP | 2000-9508 | 1/2000 |
| JP | 2003-28689 | 1/2003 |
| JP | 2007-333655 | 12/2007 |
| JP | 2009-168688 | 7/2009 |
| JP | 2009-204586 | 9/2009 |
| JP | 2009-222534 | 10/2009 |
| WO | 2008/042412 | 4/2008 |

OTHER PUBLICATIONS

Chinese Office Action issued Dec. 3, 2013 in corresponding Chinese Patent Application No. 201080064976.5 with English translation.
Extended European Search Report issued Jan. 9, 2015 in corresponding European Patent Application No. 10849865.0.
Japanese Decision of a Patent Grant issued Mar. 11, 2014 in corresponding Japanese Patent Application No. 2010-092574 with English translation.
Korean Notice of Allowance issued Apr. 22, 2014 in corresponding Korean Application No. 10-2012-7021948 with partial English translation.
International Search Report issued Feb. 1, 2011 in International (PCT) Application No. PCT/JP2010/070832.
Chinese Notice of Allowance issued Jul. 3, 2014 in corresponding Chinese Patent Application No. 201080064976.5 (with English translation).
Written Opinion of the International Searching Authority issued Feb. 1, 2011 in International (PCT) Application No. PCT/JP2010/070832 with English translation.

\* cited by examiner

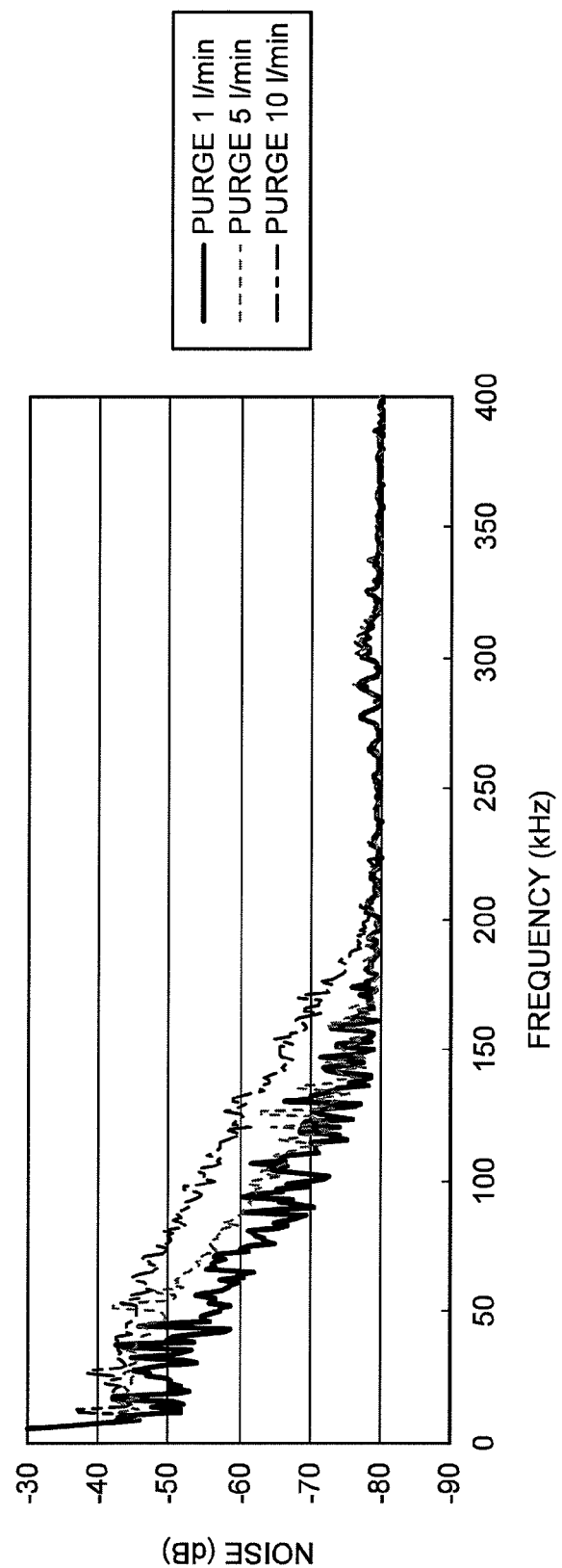

STRAIN GAUGE AMPLIFIER

FLOW VOLUME MEASUREMENT DEVICE AND FLOW VELOCITY MEASUREMENT DEVICE

FIELD

The present invention relates to a flow volume measurement device that measures a flow volume of fluid and a flow velocity measurement device that measures a flow velocity of a fluid.

BACKGROUND

As a method of measuring a flow volume of gas flowing in a flow channel, various methods have been proposed. For example, Patent Literature 1 describes a differential pressure flowmeter in which an orifice plate is arranged in a pipe, and a flow volume of fluid flowing in the pipe is measured by a pressure difference in the pipe at the front and back of the orifice plate.

Furthermore, Patent Literature 2 describes a flow volume measurement device in which a transmission element and a reception element of an ultrasonic wave are installed relative to each other with a certain angle in a flow direction of fluid, thereby measuring a flow volume of the fluid based on an ultrasonic propagation time. This flow volume measurement device includes means for oscillating an ultrasonic wave of a sinusoidal signal having frequency components of a first frequency and a second frequency that are different from each other, means for obtaining a phase difference between the first and second frequency components of the ultrasonic wave having propagated in the fluid, and means for computing an ultrasonic propagation time from the obtained phase difference. The flow volume measurement device calculates a flow velocity of the fluid from the ultrasonic propagation time to obtain the flow volume.

CITATION LIST

Patent Literatures

Patent Literature 1: Japanese Patent Application Laid-open No. H06-174510
Patent Literature 2: Japanese Patent Application Laid-open No. 2009-222534

SUMMARY

Technical Problem

In the device that measures the flow volume based on the pressure difference described in Patent Literature 1, an orifice needs to be provided inside a pipe. Therefore, a certain linear pipe portion needs to be provided at the front and back of the orifice, thereby imposing a limitation on objects to be used. In the flow volume measurement device that uses the ultrasonic wave described in Patent Literature 2, an ultrasonic generation source and a detector are directly attached to a pipe. Therefore, for example, when gas flowing in the pipe has a high temperature, the device cannot be used, or a mechanism capable of being used even under a high-temperature condition is required. The both methods described in Patent Literature 1 and Patent Literature 2 require a certain period of time for measurement, thereby causing a problem that improvement in responsiveness is limited. Furthermore, while a flow velocity can be also measured based on a relation between a diameter of the pipe and the flow volume, this measurement also has the same problem.

The present invention has been achieved to solve the above problems, and an object of the present invention is to provide a flow volume measurement device and a flow velocity measurement device that can perform measurement with high responsiveness and can perform measurement of fluid flow even under severe environments.

Solution to Problem

According to an aspect of the present invention, a flow volume measurement device includes: a measurement cell including a main pipe with opposite ends being open and connectable to a flow channel through which fluid flows, an incident tube that is connected to the main pipe and formed with a window for allowing passage of light at an end opposite to a side connected to the main pipe, an emission tube that is connected to the main pipe and formed with a window for allowing passage of light at an end opposite to a side connected to the main pipe, and a first purge-fluid supply tube that is connected to the incident tube; a purge-fluid supply unit that supplies purge fluid into the first purge-fluid supply tube of the measurement cell; a light emitting unit that emits a laser beam to the incident tube; a light receiving unit that receives the laser beam having entered from the incident tube, passed through the measurement cell, and emitted from the emission tube, and outputs a received amount of light as a light reception signal; a calculation unit that calculates a flow volume of fluid flowing in the measurement cell, based on a light reception signal output from the light receiving unit; a flow-direction detection unit that detects a flow direction of fluid flowing in the measurement cell; and a control unit that controls an operation of respective units.

Accordingly, measurement can be performed with high responsiveness, and measurement of the flow volume and the flow direction thereof can be performed even under severe environments.

Advantageously, the flow-direction detection unit includes a differential-pressure detection unit that detects a pressure difference in both directions parallel to a flow direction, and detects the flow direction based on the pressure difference detected by the differential-pressure detection unit. Accordingly, the flow direction of fluid can be detected more appropriately.

Advantageously, the flow-direction detection unit includes a deforming part that is exposed in the flow channel and deforms due to fluid flow, and detects the flow direction based on a deforming direction of the deforming part. Accordingly, the flow direction of fluid can be detected more appropriately.

Advantageously, at least two measurement units including the light emitting unit, the light receiving unit, and the calculation unit are provided. The flow-direction detection unit detects the flow direction based on calculation values of a flow volume calculated by the measurement units. Accordingly, the flow direction of fluid can be detected more appropriately.

Advantageously, the flow-direction detection unit includes an ultrasonic output unit that outputs an ultrasonic wave to the flow channel and an ultrasonic reception unit that receives the ultrasonic wave output from the ultrasonic output unit, and detects the flow direction based on a frequency of the ultrasonic wave received by the ultrasonic reception unit. Accordingly, the flow direction of fluid can be detected more appropriately.

Advantageously, the calculation unit demodulates a light reception signal received by the light receiving unit by one frequency, and calculates a flow volume of the fluid based on a magnitude of a fluctuation in the demodulated signal. Accordingly, the flow volume can be measured with a simple configuration by using a fluctuation in a signal modulated by one frequency.

Advantageously, the calculation unit respectively demodulates a light reception signal received by the light receiving unit by two different frequencies, and calculates a flow volume of the fluid based on a magnitude of a fluctuation in the demodulated signal in two frequencies. Accordingly, the flow volume can be measured with higher accuracy.

Advantageously, the calculation unit respectively demodulates a light reception signal received by the light receiving unit by a plurality of different frequencies, and calculates a flow volume of the fluid based on a magnitude of a fluctuation in the demodulated signal in the frequencies. Accordingly, the flow volume can be measured with higher accuracy.

Advantageously, the calculation unit stores therein a relation between a calculated fluctuation and flow volume in advance, and calculates the flow volume of the fluid based on the relation and the magnitude of the fluctuation. Accordingly, the flow volume can be measured more easily.

Advantageously, the calculation unit stores therein a relation between the calculated fluctuation and the flow volume of the fluid for each flow volume of purge fluid flowing in the incident tube, and calculates the flow volume of the fluid based on the flow volume of purge fluid flowing in the incident tube and the fluctuation. Accordingly, the flow volume can be measured with higher accuracy.

Advantageously, the control unit calculates the flow volume of the purge fluid, in which an amount of change in the fluctuation increases in an area including the flow volume of the fluid calculated by the calculation unit, and adjusts the flow volume of the purge fluid to be supplied from the purge-fluid supply unit to the first purge-fluid supply tube based on a calculation result thereof. Accordingly, the flow volume can be measured with higher accuracy.

Advantageously, the calculation unit also calculates a concentration of a substance to be measured in exhaust fluid flowing in the measurement cell based on an intensity of the laser beam output from the light emitting unit and an intensity of the laser beam received by the light receiving unit. Accordingly, more pieces of information can be acquired for the flowing fluid.

Advantageously, the light receiving unit includes a plurality of light receiving elements arranged adjacent to each other, and outputs an amount of light received by each light receiving element as a light reception signal, and the calculation unit calculates the flow volume of the fluid based on a comparison of intensities of light reception signals transmitted from the respective light receiving elements. Also by this method, the flow volume can be measured with higher accuracy.

Advantageously, the calculation unit calculates a reached position of the laser beam based on the comparison of intensities of light reception signals transmitted from the respective light receiving elements, and calculates the flow volume of the fluid based on a misalignment between the reached position and a reference position. Accordingly, displacement of the laser beam can be detected, thereby enabling to measure the flow volume.

Advantageously, the calculation unit also calculates a concentration of a substance to be measured in exhaust fluid flowing in the measurement cell based on a sum total of intensities of light reception signals transmitted from the respective light receiving units and an intensity of the laser beam received by the light receiving unit. Accordingly, more pieces of information can be acquired for the flowing fluid.

Advantageously, the measurement cell includes a turbulence generation unit that generates turbulence in air flow near the incident tube, in an upstream of the incident tube in a flow direction of the fluid in the main pipe and near the incident tube. Accordingly, a change in the light reception signal with respect to a change in the flow volume can be increased, thereby enabling to measure the flow volume with higher accuracy.

Advantageously, a second purge-fluid supply tube that is connected to the emission tube is further included. The purge-fluid supply unit supplies purge fluid also to the second purge-fluid supply tube. Accordingly, a possibility of a window provided in the emission tube being contaminated can be reduced.

Advantageously, the calculation unit measures a flow velocity of the fluid flowing in the main pipe of the measurement cell based on a light reception signal output from the light receiving unit. Accordingly, more pieces of information of the fluid flowing in the measurement cell can be acquired.

Advantageously, the fluid is a gaseous matter.

According to another aspect of the present invention, a flow velocity measurement device includes: a measurement cell including an incident tube with one end being an opening facing a measurement area and the other end being formed with a window for allowing passage of light, an emission tube with one end being an opening opposite to the incident tube and facing the measurement area, and the other end being formed with a window for allowing passage of light, and a first purge-fluid supply tube that is connected to the incident tube; a purge-fluid supply unit that supplies purge fluid into the first purge-fluid supply tube of the measurement cell; a light emitting unit that emits a laser beam to the incident tube; a light receiving unit that receives the laser beam having entered from the incident tube, passed through the measurement area, and emitted from the emission tube, and outputs a received amount of light as a light reception signal; a calculation unit that calculates a flow velocity of fluid flowing in the measurement area, based on a light reception signal output from the light receiving unit; a flow-direction detection unit that detects a flow direction of fluid flowing in the measurement area; and a control unit that controls an operation of respective units.

Accordingly, measurement can be performed with high responsiveness, and measurement of the flow velocity and the flow direction thereof can be performed even under severe environments.

Advantageously, the flow-direction detection unit includes a differential-pressure detection unit that detects a pressure difference in both directions parallel to a flow direction, and detects the flow direction based on the pressure difference detected by the differential-pressure detection unit. Accordingly, the flow direction of fluid can be detected more appropriately.

Advantageously, the flow-direction detection unit includes a deforming part that is exposed in the measurement area and deforms due to fluid flow, and detects a flow direction based on a deforming direction of the deforming part. Accordingly, the flow direction of fluid can be detected more appropriately.

Advantageously, the measurement cell is respectively connected to one end of the incident tube and one end of the emission tube, and has a main pipe through which fluid to be measured flows, and the measurement area is a part of the main pipe. Accordingly, the flow of a measurement object can be under control, and measurement can be performed with higher accuracy.

Advantageously, the fluid is a gaseous matter.

Advantageous Effects of Invention

The flow volume measurement device and the flow velocity measurement device according to the present invention can perform measurement with high responsiveness and can perform measurement of fluid flow even under severe environments.

BRIEF DESCRIPTION OF DRAWINGS

FIG. 8 is a graph of a relation between a frequency and noise.

DESCRIPTION OF EMBODIMENTS

An embodiment of a flow volume measurement device and a flow velocity measurement device according to the present invention will be explained below in detail with reference to the accompanying drawings. The present invention is not limited to the embodiment. The flow volume measurement device can measure a flow volume and a flow velocity of fluid such as various kinds of gaseous matter (gas) and liquids flowing in a flow channel. For example, the flow volume measurement device can be attached to a diesel engine to measure a flow volume of flue gas discharged from the diesel engine. An engine that discharges flue gas, that is, a device that discharges (supplies) gas to be measured is not limited thereto, and the flow volume measurement device can be used for various internal combustion engines such as a gasoline engine and a gas turbine. Furthermore, as a device having an internal combustion engine, various devices such as vehicles, ships and vessels, and power generators can be exemplified. Further, a flow volume and a flow velocity of flue gas discharged from burning appliances such as an incinerator and a boiler and flow-volume and flow-velocity measurement objects having a high temperature and fluctuations in the flow volume and the flow velocity can be measured. In the following embodiments, a case of measuring a flow volume of flue gas flowing in a pipe is explained. Further, a flow velocity of flue gas flowing in the pipe can be also measured by a device configuration of the flow volume measurement device described in the following embodiments, as described later.

Figure 1:
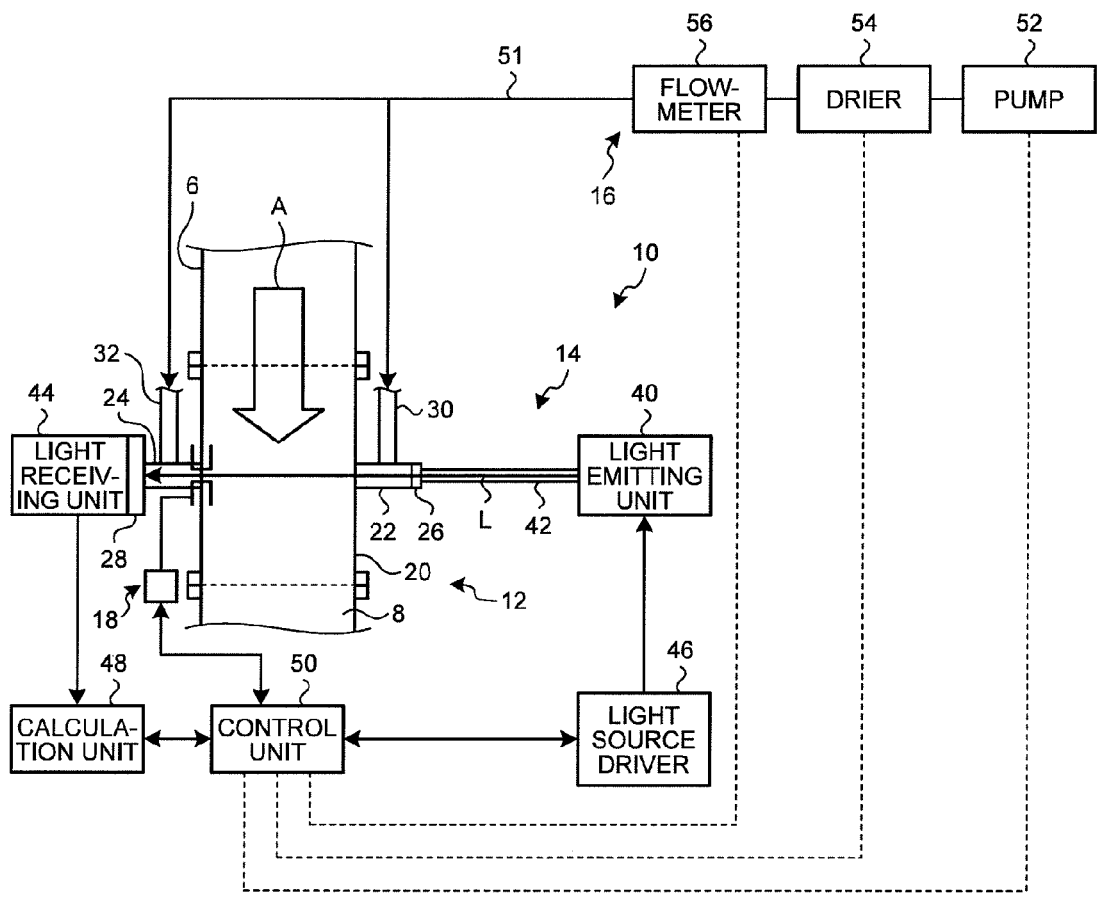
FIG. 1 is a pattern diagram of a schematic configuration of a flow volume measurement device according to an embodiment of the present invention.
Figure 2:
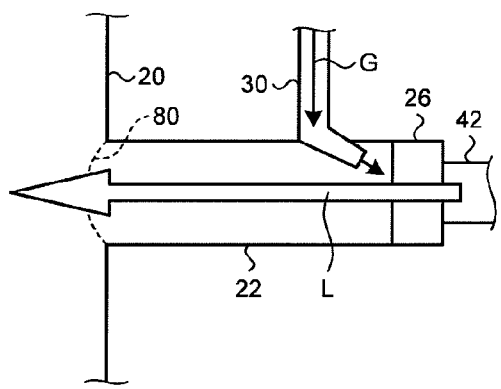
FIG. 2 is an enlarged pattern diagram of a part of a measurement cell of the flow volume measurement device shown in FIG. 1 in an enlarged manner.

FIG. 1 is a pattern diagram of a schematic configuration of a flow volume measurement device according to an embodiment of the present invention. FIG. 2 is an enlarged pattern diagram of a part of a measurement cell of the flow volume measurement device shown in FIG. 1 in an enlarged manner. As shown in FIG. 1, a flow volume measurement device 10 includes a measurement cell 12, a measurement means 14, a purge-gas supply means 16, and a flow-direction detection means 18. The flow volume measurement device 10 is provided between a pipe 6 and a pipe 8, through which flue gas A flows. The flue gas A is supplied from an upstream side of the pipe 6, passes through the pipe 6, the flow volume measurement device 10, and the pipe 8, and is discharged to a downstream side of the pipe 8. A flue-gas generation device (a supply device) is arranged on the upstream side of the pipe 6.

The measurement cell 12 basically includes a main pipe 20, an incident tube 22, and an emission tube 24. The incident tube 22 is provided with a window 26 and a purge-gas supply pipe 30, and the emission tube 24 is provided with a window 28 and a purge-gas supply pipe 32. The main pipe 20 is a cylindrical tubular member, with one end thereof being connected to the pipe 6 and the other end being connected to the pipe 8. That is, the main pipe 20 is arranged at a position being a part of a flow channel through which the flue gas A flows. Accordingly, the flue gas A flows in the pipe 6, the main pipe 20, and the pipe 8 in this order. Furthermore, all the flue gas A flowing in the pipe 6 basically flows in the main pipe 20.

The incident tube 22 is a tubular member, with one end thereof being connected to the main pipe 20. In the main pipe 20, a connection part with the incident tube 22 has an opening having substantially the same shape as that of an opening (an opening at an end) of the incident tube 22. That is, the incident tube 22 is connected to the main pipe 20 in a state capable of circulating air. The window 26 is provided at the other end of the incident tube 22, and the incident tube 22 is sealed by the window 26. The window 26 is made of a member that transmits light, for example, transparent glass or resin. Accordingly, the incident tube 22 is in such a state that the end provided with the window 26 does not circulate air but allows passage of light.

As shown in FIGS. 1 and 2, the incident tube 22 has a cylindrical shape in which an area of the opening at the end on a side of the window 26 (that is, the opening blocked by the window 26) and an area of the end on a side of the main pipe 20 (that is, an opening of a portion connected to the main pipe 20) are substantially the same. The shape of the incident tube 22 is not limited to the cylindrical shape, and can be various shapes so long as it is a barrel shape capable of allowing passage of air and light. For example, the incident tube 22 can have a cross-section in a tetragonal, polygonal, or ellipsoidal shape, or a shape of an asymmetric curved surface. Furthermore, the incident tube 22 can have a cylindrical cross-sectional shape or a shape with a diameter being changed according to a position. It is preferred that the incident tube 22 have a shape capable of allowing purge gas to flow stably.

The incident tube 22 is connected with the purge-gas supply pipe 30. As shown in FIG. 2, the purge-gas supply pipe 30 is arranged between the end of the incident tube 22 sealed by the window 26 and the other end connected to the main pipe 20. The purge-gas supply pipe 30 guides purge gas supplied from the purge-gas supply means 16 to the incident tube 22. Further, a portion of the purge-gas supply pipe 30, which becomes an outlet of purge gas, is inclined toward the window 26.

The emission tube 24 is a tubular member having substantially the same shape as that of the incident tube 22, with one end thereof being connected to the main pipe 20 and the other end thereof being provided with the window 28. The emission tube 24 is also in such a state that air can be circulated between the main pipe 20 and the emission tube 24, and the end provided with the window 28 does not circulate air but allows passage of light. Further, a central axis of the emission tube 24 is arranged at a position substantially the same as that of a central axis of the incident tube 22. That is, the incident tube 22 and the emission tube 24 are arranged at positions of the main pipe 20 opposite to each other.

The emission tube 24 has also a cylindrical shape in which an area of the opening at the end on a side of the window 28 (that is, the opening blocked by the window 28) and an area of the end on a side of the main pipe 20 (that is, an opening of a portion connected to the main pipe 20) are substantially the same. The shape of the emission tube 24 is not limited to the cylindrical shape, and can be various shapes so long as it is a barrel shape capable of allowing passage of air and light. For example, the emission tube 24 can have a cross-section in a tetragonal, polygonal, or ellipsoidal shape, or a shape of an asymmetric curved surface. The emission tube 24 can have a cylindrical cross-sectional shape or a shape with a diameter being changed according to a position. It is preferred that the emission tube 24 also have a shape capable of allowing purge gas to flow stably.

The purge-gas supply pipe 32 is arranged between the end of the emission tube 24 sealed by the window 28 and the other end connected to the main pipe 20. The purge-gas supply pipe 32 guides purge gas supplied from the purge-gas supply means 16 to the emission tube 24. The purge-gas supply pipe 32 has such a shape that an outlet is directed toward the window 28. A part of the flow-direction detection means 18 described later is arranged in the emission tube 24.

The measurement means 14 includes a light emitting unit 40, an optical fiber 42, a light receiving unit 44, a light source driver 46, a calculation unit 48, and a control unit 50.

The light emitting unit 40 is a light emitting element that emits a laser beam of a predetermined wavelength. The optical fiber 42 guides the laser beam output from the light emitting unit 40 to enter into the measurement cell 12 from the window 26.

The light receiving unit 44 receives the laser beam having passed through the inside of the main pipe 20 of the measurement cell 12 and output from the window 28 of the emission tube 24. The light receiving unit 44 includes, for example, a photodetector such as a photodiode (PD), to receive a laser beam by the photodetector and detects an intensity of the light. The light receiving unit 44 transmits the intensity (an amount of light) of the received laser beam to the calculation unit 48 as a light reception signal.

The light source driver 46 has a function of controlling drive of the light emitting unit 40, and adjusts the wavelength and intensity of the laser beam output from the light emitting unit 40 by adjusting current and voltage to be supplied to the light emitting unit 40. The light source driver 46 is controlled by the control unit 50.

The calculation unit 48 calculates a flow volume of flue gas flowing in the measurement cell 12 based on an intensity signal (a light reception signal) of the laser beam received by the light receiving unit 44. A calculation method thereof is explained later.

The control unit 50 has a control function of controlling operations of respective units, and controls the operations of respective units according to need. The control unit 50 controls not only the measurement means 14 but also the entire operation of the flow volume measurement device 10. That is, the control unit 50 controls the operation of the flow volume measurement device 10.

The purge-gas supply means 16 includes a pipe 51, a pump 52, a drier 54, and a flowmeter 56, and supplies a predetermined amount of air to the purge-gas supply pipes 30 and 32 of the measurement cell 12. In the present embodiment, air is supplied; however, nitrogen or the like can be supplied as purge gas by using a cylinder.

The pipe 51 is connected to the purge-gas supply pipes 30 and 32. The pump 52, the drier 54, and the flowmeter 56 are arranged in the pipe 51 sequentially from the farthest side of the purge-gas supply pipes 30 and 32 (an upstream of air flow). The pump 52 supplies air to the pipe 51, thereby supplying air to the purge-gas supply pipes 30 and 32. The operation of the pump 52 is controlled by the control unit 50.

The drier 54 is a drying mechanism that dries air flowing in the pipe 51. The drier 54 needs only to decrease moisture contained in the air, and various moisture absorption mechanisms and moisture absorbent materials can be used. The operation of the drier 54 is controlled by the control unit 50.

The flowmeter 56 measures an amount of air flowing in the pipe 51, that is, the flow volume. The flowmeter 56 transmits information of the measured flow volume to the control unit 50. Because air fed from the pump 52 basically passes through the pipe 51, the flow volume is stable. Therefore, various flowmeters generally used can be used.

The purge-gas supply means 16 controls the amount of air flowing in the pipe 51, because the control unit 50 controls the flow volume of purge gas based on a measurement result acquired by the flowmeter 56. Accordingly, the purge-gas supply means 16 can set the amount of air and the flow velocity thereof supplied from the purge-gas supply pipe 30 to the incident tube 22, and the amount of air and the flow velocity thereof supplied from the purge-gas supply pipe 32 to the emission tube 24, respectively, to a predetermined amount and velocity. Furthermore, because the drier 54 dries the air, a possibility of moisture adhering to the flowmeter 56 can be reduced. The flow volume measurement device 10 has the configuration described above.

Figure 3:
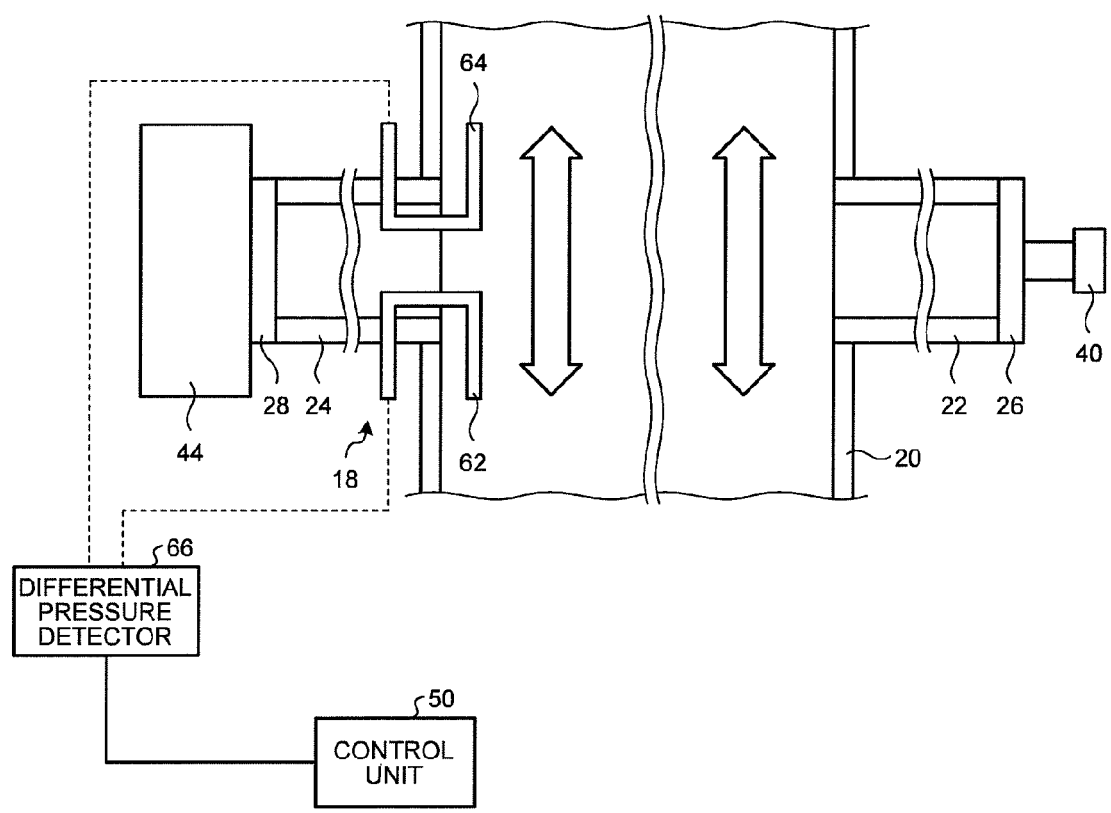
FIG. 3 is a pattern diagram of a schematic configuration of a flow-direction detection means shown in FIG. 1.

The flow-direction detection means 18 is explained next with reference to FIG. 3. FIG. 3 is a pattern diagram of a schematic configuration of the flow-direction detection means shown in FIG. 1. The flow-direction detection means 18 detects a flow direction of the flue gas A in the main pipe 20, and as shown in FIG. 3, includes a detection element 62, a detection element 64, and a differential pressure detector (a differential pressure transducer) 66. The detection element 62 is a pitot tube that detects pressure of the flue gas A in one direction (in the present embodiment, a direction from an outlet of the pipe 8 toward a flue gas generation device, a direction from downstream to upstream in a fundamental flow direction), of directions parallel to an axial direction of the main pipe 20 (directions parallel to a flow direction of the flue gas A). The detection element 62 has a U-shape, in which one end is exposed to the inside of the main pipe 20 and is open to the outlet of the pipe 8.

The detection element 64 is also a pitot tube that detects pressure of the flue gas A in the other direction (in the present embodiment, a direction from the flue gas generation device toward the outlet of the pipe 8, a direction from upstream to downstream in the fundamental flow direction), of directions parallel to the axial direction of the main pipe 20. The detection element 64 has a U-shape, in which one end is exposed to the inside of the main pipe 20 and is open to the flue gas generation device.

The detection element 62 and the detection element 64 are respectively arranged in a connection part between the main pipe 20 and the emission tube 24. Furthermore, in the fundamental flow direction of the flue gas A, the detection element 62 is arranged on a downstream side of the detection element 64, that is, on the outlet side of the pipe 8. In this manner, the detection element 62 and the detection element 64 are symmetrically arranged with respect to a plane orthogonal to the flow direction of the flue gas A as a plane of symmetry. In the present embodiment, the pitot tube is used as the detection elements 62 and 64. However, the detection elements 62 and 64 need only to detect the pressure of flue gas in a predetermined direction and are not limited to the pitot tube.

The differential pressure detector 66 receives a detection value detected by the detection element 62 and a detection value detected by the detection element 64 and converts the detection values to pressure values, to calculate a pressure difference. The differential pressure detector 66 further detects a flow direction of the flue gas A based on the detected pressure value. Specifically, the flow-direction detection means 18 detects the pressure of the flue gas A flowing from the outlet of the pipe 8 toward the flue-gas generation device by the detection element 62, and detects the pressure of the flue gas A flowing from the flue-gas generation device toward the outlet of the pipe 8 by the detection element 64. Thereafter, the differential pressure detector 66 calculates a pressure difference based on the detection values (detected pressures), to calculate which is larger the pressure detected by the detection element 62 or the pressure detected by the detection element 64. The differential pressure detector 66 detects a flow direction of flue gas detected by the detection element that has detected the larger pressure as the flow direction of the flue gas A based on these detection results. That is, when the pressure detected by the detection element 62 is larger, the flow-direction detection means 18 detects that flue gas is flowing from downstream to upstream, that is, from the outlet of the pipe 8 toward the flue-gas generation device. When the pressure detected by the detection element 64 is larger, the flow-direction detection means 18 detects that flue gas is flowing from upstream to downstream, that is, from the flue-gas generation device toward the outlet of the pipe 8. The differential pressure detector 66 transmits information of the detected flow direction of the flue gas A to the control unit 50. A part of calculation performed by the differential pressure detector 66 can be performed by the control unit 50.

A method of measuring a flow volume carried out by the flow volume measurement device 10 is explained below with respective to FIGS. 2 and 4. First, the measurement means 14 of the flow volume measurement device 10 causes the light emitting unit 40 to emit a laser beam L. The emitted laser beam L passes through the optical fiber 42, the window 26, the incident tube 22, the main tube 20, the emission tube 24, and the window 28 in this order, and enters into the light receiving unit 44. At this time, the flow volume measurement device 10 supplies purge gas G from the purge-gas supply pipe 30 to the incident tube 22 by the purge-gas supply means 16, and also supplies the purge gas G from the purge-gas supply pipe 32 to the emission tube 24. Accordingly, it is suppressed that the flue gas A enters into the incident tube 22 and the emission tube 24, and that fine particles contained in the flue gas A adheres to the windows 26 and 28.

The purge gas G supplied by the purge-gas supply means 16 and the flue gas A flowing in the main pipe 20 are air having a different property, specifically, the temperature of the gas is different. Therefore, as shown in FIG. 2, the present inventors have found that a temperature boundary layer 80 is formed in a region where the purge gas G that is supplied from the purge-gas supply means 16, passes through the incident tube 22, and reaches the main pipe 20 and the flue gas A flowing in the main pipe 20 are mixed. Furthermore, because the temperatures of the purge gas G and the flue gas A are different, putting the temperature boundary layer 80 therebetween as a boundary, refractive indexes thereof have different values.

Figure 4:
FIG. 4 is an explanatory diagram for explaining a path of a laser beam.

Therefore, as shown in FIG. 4, the laser beam L is refracted by passing through the temperature boundary layer 80. FIG. 4 is an explanatory diagram for explaining a path of the laser beam. For example, as shown in FIG. 4, if it can be assumed that the temperature boundary layer 80 is inclined by $\theta 1$ with respect to a traveling direction of the laser beam L, the laser beam L has an angle of $\theta 2$ between the temperature boundary layer 80 and the laser beam L by passing through the temperature boundary layer 80. Accordingly, the traveling direction of light changes by a difference between $\theta 1$ and $\theta 2$, thereby changing a reached position.

The temperature boundary layer 80 is unstable. Therefore, an angle of a layer that can be regarded as the temperature boundary layer 80 changes from moment to moment, and the reached position of the laser beam L also changes from moment to moment. If the reached position changes, a position at which the light receiving unit 44 receives the laser beam L changes. That is, a measurement condition changes. The change in the reached position of the laser beam L appears as noise (a signal fluctuation) in a demodulation result of the light reception signal received by the light receiving unit 44. The signal fluctuation becomes noise at the time of measuring other physical values. However, in the present invention, the signal fluctuation becomes a value of a measurement object for obtaining the flow volume. In the explanations of the present embodiment, the signal fluctuation is referred to as noise for convenience' sake.

The present inventors have found that there is a correlation between noise and the flow volume flowing in the main pipe

20, as a result of intensive study of noise. The flow volume measurement device 10 calculates the flow volume based on the relation.

Figure 5:
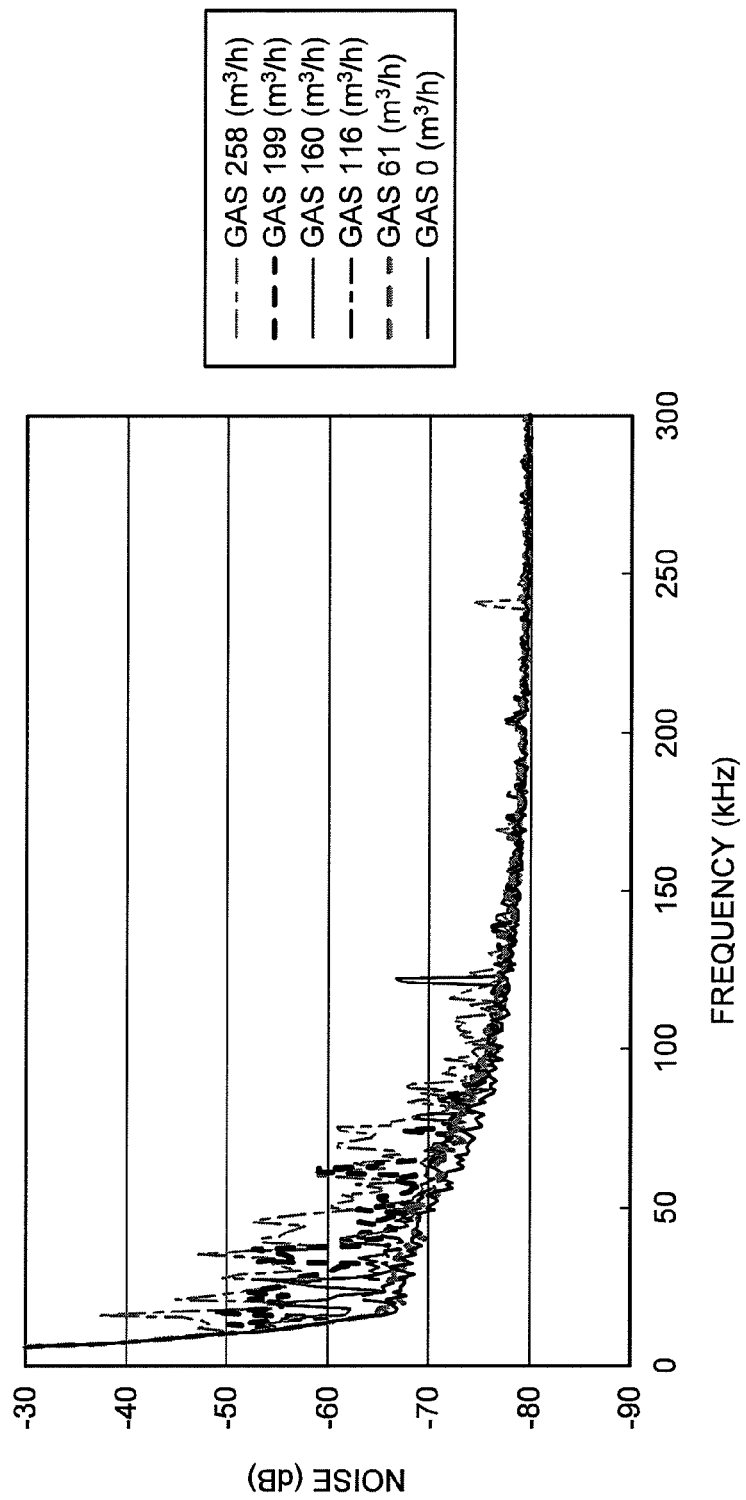
FIG. 5 is a graph of a relation between a frequency and noise.
Figure 6:
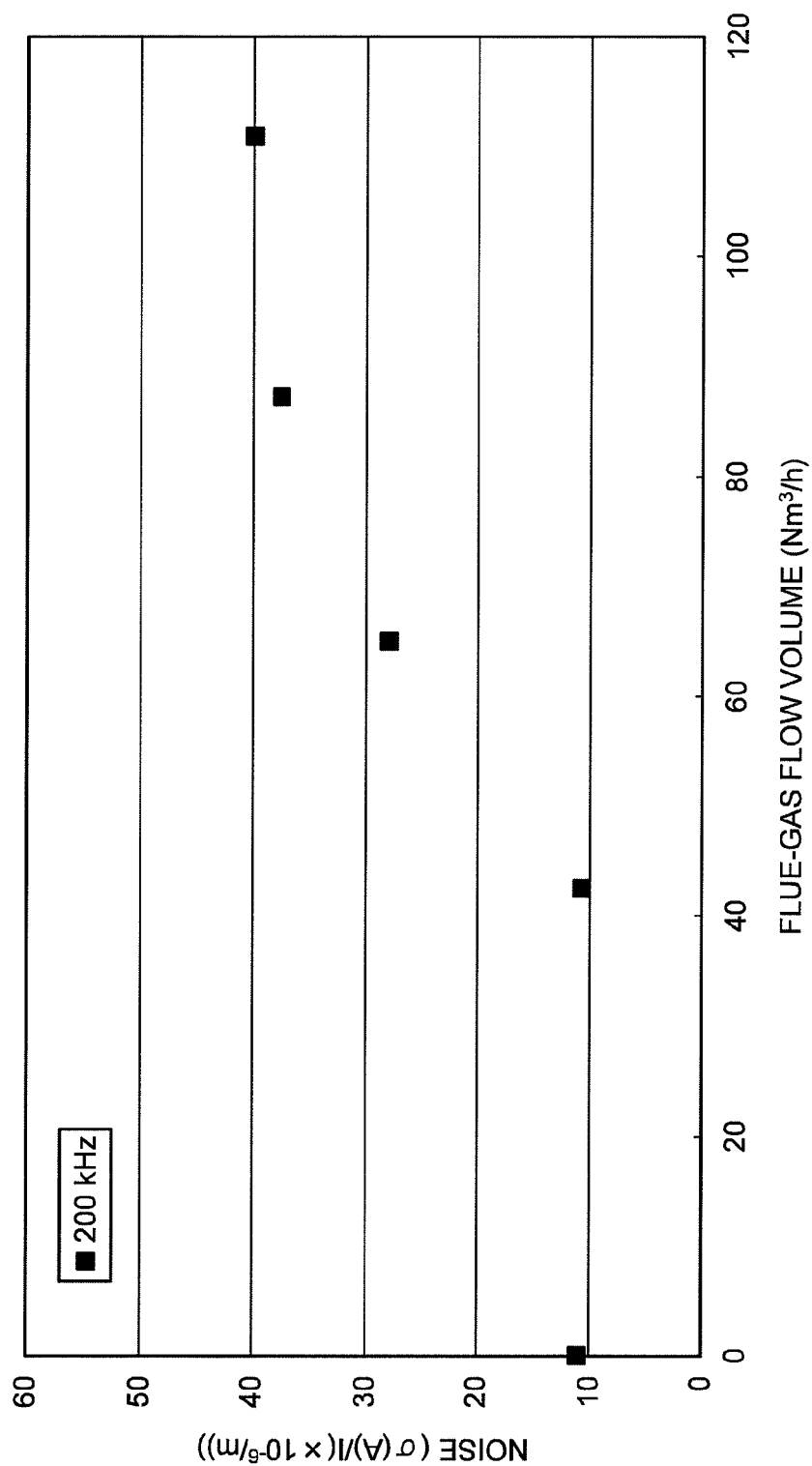
FIG. 6 is a graph of a relation between a flue-gas flow volume and noise.

The method of measuring the flow volume performed by the flow volume measurement device 10 is explained below in detail with reference to FIGS. 5 and 6. First, the flow volume of flue gas was changed to various values, and a light reception signal was demodulated by various frequencies for each flow volume of flue gas to measure a relation between a demodulation frequency and noise as a result of demodulation. In this measurement, the relation between the demodulation frequency and noise was measured for cases where the flow volume of flue gas was 0 (that is, flue gas was not caused to flow), 61 m$^3$/h, 116 m$^3$/h, 160 m$^3$/h, 199 m$^3$/h, and 258 m$^3$/h, respectively. These measurement processes were performed under the same conditions except for changing the flow volume of flue gas. The measurement results are shown in FIG. 5. FIG. 5 is a graph of a relation between a frequency and noise. In FIG. 5, a vertical axis represents noise (decibels) and a horizontal axis represents a frequency (kilohertz). The frequency indicates a frequency used for demodulating the light reception signal received by the light receiving unit 44. As shown in FIG. 5, it is understood that a magnitude of generated noise changes according to the flow volume of flue gas. Basically, noise increases with an increase in the flow volume of flue gas.

The relation between noise and a flue-gas flow volume (a flow volume of flue gas) in the case of a demodulation frequency being 200 kilohertz was calculated based on the measurement results. A calculation result is shown in FIG. 6. FIG. 6 is a graph of a relation between a flue-gas flow volume and noise. In FIG. 6, noise ($\sigma(A)/I(\times 10^{-6}/m)$) was plotted on a vertical axis and the flue-gas flow volume (Nm$^3$/h) was plotted on a horizontal axis. As shown in FIG. 6, a magnitude of noise changes according to the flow volume of flue gas at the demodulation frequency of flow velocity measurement device 200 kilohertz.

The flow volume measurement device 10 calculates the flow volume based on the magnitude of noise by using the above relation. Specifically, the relation between the magnitude of noise and the flow volume of flue gas as shown in FIG. 6 is calculated in advance by experiments and measurement, which is stored in the calculation unit 48. The calculation unit 48 demodulates the light reception signal transmitted from the light receiving unit 44 by a frequency of 200 kilohertz, and detects the magnitude of noise in the demodulation result (signal). Thereafter, the flow volume measurement device 10 calculates the flow volume of flue gas based on the stored relation between the magnitude of noise and the flow volume of flue gas.

In this manner, the flow volume measurement device 10 can calculate the flow volume in the pipe based on noise generated at the time of demodulation of the light reception signal of the light receiving unit 44 that has received the laser beam L emitted from the light emitting unit 40. Furthermore, because the laser beam is used for measurement, measurement can be performed in a short time. Specifically, by using light, the time required from emission of light until reception of light can be made shorter than that when using a sound wave or the like. Further, the measurement time and the calculation time required for calculating noise can be made short. Accordingly, responsiveness can be increased. Further, the flow volume can be calculated continuously.

Furthermore, because light can be guided by an optical fiber or the like, the light emitting unit and the light receiving unit do not need to be provided directly in the pipe. Therefore, electronic parts (a circuit and the like) do not need to be placed under severe conditions, and can be used under various environments. For example, the flow volume of flue gas flowing in the pipe, which becomes a high temperature, can be measured.

In the above embodiment, the light reception signal is demodulated by a frequency of 200 kilohertz as an example. However, the present invention is not limited thereto, and an arbitrary frequency can be used for the frequency used for demodulation. Further, as a method of demodulating the light reception signal by the calculation unit, various configurations can be used. For example, the light reception signal can be demodulated by a predetermined frequency component by extracting a target frequency component by using a band-pass filter that allows passage of only a specific frequency component. When the band-pass filter is used, a device configuration can be simplified, and low device cost can be realized. Further, computation performed for calculating the flow volume can be reduced. Decoding can be performed by using a FFT (Fast Fourier Transform) computing device or a spectrum analyzer. When the FFT computing device or the spectrum analyzer is used, demodulation of the light reception signal can be performed over a certain frequency domain.

In the above embodiment, the flow volume is calculated based on noise in a light reception signal demodulated by one frequency (200 kilohertz) (that is, one frequency component in a demodulation result of the light reception signal). However, the present invention is not limited thereto. The flow volume measurement device can calculate the flow volume based on noise in a light reception signal demodulated by two different frequencies (that is, two frequency components in a demodulation result of the light reception signal).

Figure 7:
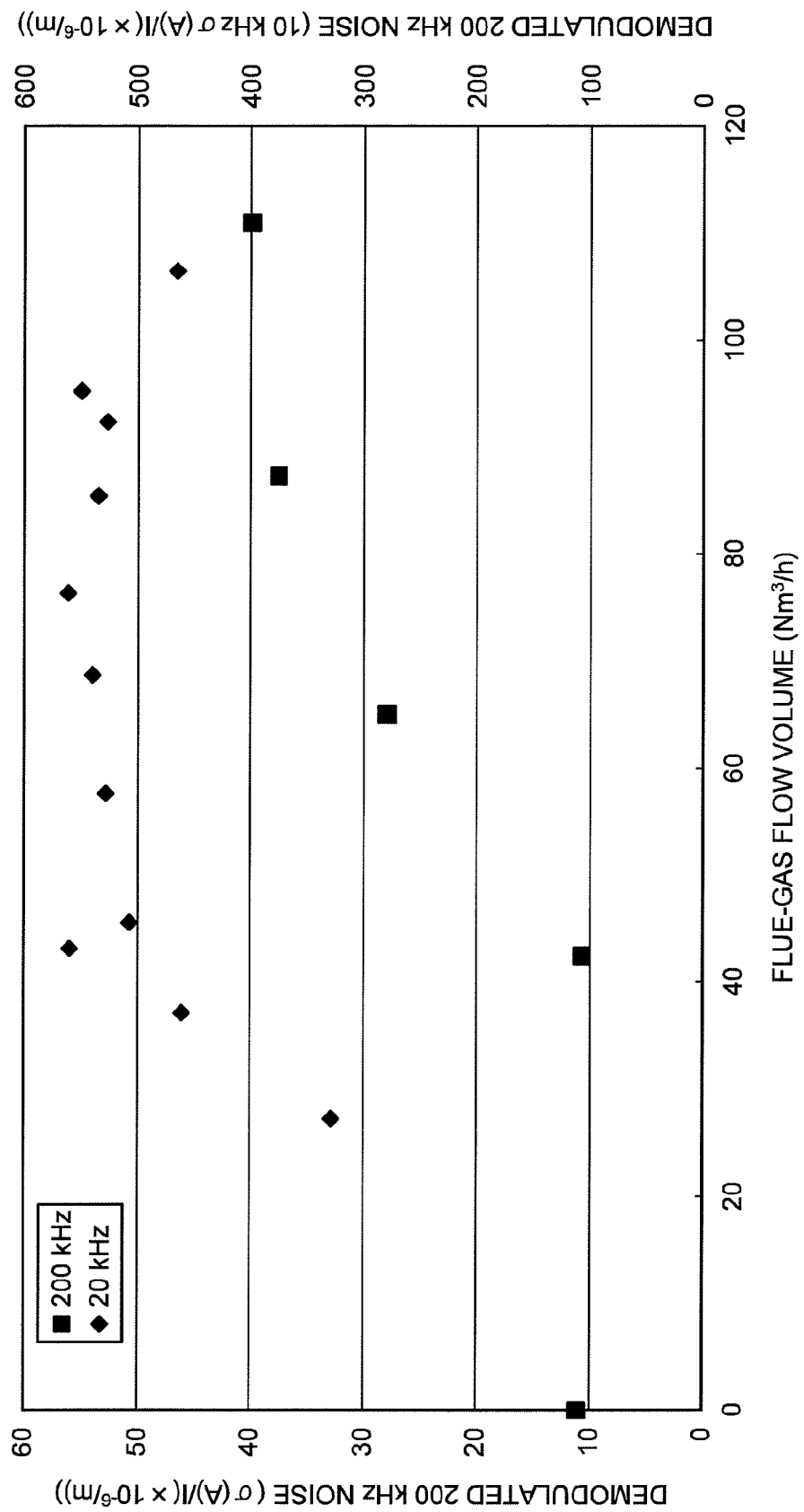
FIG. 7 is a graph of a relation between a flue-gas flow volume and noise.

A case where the flow volume is calculated based on noise in a light reception signal demodulated by two different frequencies is explained below with reference to FIG. 7. In an example shown in FIG. 7, a relation between noise at the time of demodulating a light reception signal by a frequency of 200 kilohertz and a flow volume of flue gas, and a relation between noise at the time of demodulating a light reception signal by a frequency of 20 kilohertz and a flow volume of flue gas are used. FIG. 7 is a graph of a relation between a flue-gas flow volume (a flow volume of flue gas) and noise. In FIG. 7, a vertical axis represents noise ($\sigma(A)/I(\times 10^{-6}/m)$) when decoding is performed by 200 kilohertz, and noise (10 kHz$\sigma$(A)/I($\times 10^{-6}$/m)) when decoding is performed by 20 kilohertz and a horizontal axis represents the flue-gas flow volume (Nm$^3$/h). The relation between noise and a flow volume of flue gas shown in FIG. 7 can be also calculated based on the measurement result shown in FIG. 5.

The flow volume measurement device 10 calculates the relation between the magnitude of noise and the flow volume of flue gas as shown in FIG. 7 in advance by experiments and measurement, which is stored in the calculation unit 48. The calculation unit 48 demodulates the light reception signal transmitted from the light receiving unit 44 by a frequency of 200 kilohertz and a frequency of 20 kilohertz, and detects the magnitude of noise in the demodulation result (signal) for each frequency. Thereafter, the flow volume measurement device 10 calculates the flow volume of flue gas based on the stored relation between the two magnitudes of noise and the flow volume of flue gas. In this manner, the flow volume of flue gas can be measured by using two frequency components.

As shown in FIG. 7, a flow volume at which the magnitude of noise largely changes is different according to the frequency used for demodulation. Specifically, when demodulation is performed by using a frequency of 200 kilohertz, the magnitude of noise does not change if the flow volume of flue gas is equal to or less than 40 Nm³/h. However, noise largely changes in a range of a flow volume from 50 Nm³/h to 90 Nm³/h. Furthermore, when demodulation is performed by using a frequency of 20 kilohertz, the magnitude of noise largely changes if the flow volume is equal to or less than 60 Nm³/h. However, the magnitude of noise hardly changes in a range of a flow volume from 60 Nm³/h to 100 Nm³/h. In this manner, the easily detectable range of a flow volume is different according to the frequency. Accordingly, the flow volume can be calculated with high accuracy by using a plurality of frequencies to perform demodulation and calculating the flow volume by using the detection results. The flow volume measurement device 10 can switch the demodulation frequency to be used for obtaining a calculation result according to the flow volume of flue gas.

For example, when the calculated flow volumes are different between the flow volume of flue gas calculated based on noise by 200 kilohertz and the flow volume of flue gas calculated based on noise by 20 kilohertz, the priority is determined according to the magnitude of the flow volume, and a measurement result having a higher priority is designated as the flow volume of flue gas. Specifically, when the flow volume in the calculation result is equal to or less than 60 Nm³/h, the flow volume calculated based on noise in the result acquired by performing demodulation by the frequency of 20 kilohertz is used. When the flow volume in the calculation result is more than 60 Nm³/h, the flow volume calculated based on noise in the result acquired by performing demodulation by the frequency of 200 kilohertz is used. A correlation between the two calculation results can be used for calculation. Alternatively, a mean value can be used as a calculation value.

The flow volume measurement device 10 can detect a flow direction of the flue gas A by the flow-direction detection means 18. Accordingly, even if the flue gas A is pulsing, it can be accurately ascertained in which direction the flue gas A is moving. Accordingly, the flow volume measurement device 10 can calculate the flow direction of the flue gas A in addition to the flow volume of the flue gas A, and can determine the flow of the flue gas A in the main pipe 20 more accurately.

In the present embodiment, a part of the detection element 62 and a part of the detection element 64 are arranged in the emission tube 24. However, the present invention is not limited thereto. It is preferred that the detection element 62 and the detection element 64 be arranged at positions different from positions of the incident tube 22 and the emission tube 24 in a circumferential direction. By arranging the detection elements 62 and 64 at positions different from those of the incident tube 22 and the emission tube 24, the influence of the detection elements 62 and 64 on the measurement by the measurement means 14 can be reduced. It is preferred that the detection elements 62 and 64 be arranged at the same positions as those of the incident tube 22 and the emission tube 24 in an axial direction of the main pipe 20. Accordingly, a measurement position of the flow-direction detection means 18 can be set to the same position as the measurement position of the measurement means 14.

When the light reception signal is demodulated by two frequencies, for example, two band-pass filters need only to be provided.

The number of frequencies used for demodulation is not limited to two, and the number thereof is not particularly limited. When two or more demodulation results by the frequency are used, the flow volume of flue gas can be calculated based on a correlation of measurement results. That is, a relation between noise and a flow volume is calculated for each case of demodulation by each frequency, and a plurality of calculation results are relatively compared to calculate the flow volume of flue gas. In this manner, by increasing the number of frequencies used for demodulation, the flow volume of flue gas can be calculated with higher accuracy. When decoding is performed by using the plurality of frequencies, a band-pass filter can be provided for each frequency used for decoding. However, demodulation can be performed by analyzing a light reception wavelength in a certain wavelength region by using the FFT computing device or the spectrum analyzer described above. When the frequency used for demodulation can be changed over (adjusted), it is preferred to increase a purge flow volume when the flow volume of flue gas is small (at the time of a low flow volume), and to decrease the purge flow volume when the flow volume of flue gas is large (at the time of a high flow volume). Accordingly, the measurement sensitivity can be increased. As the flow volume to be determined, a flow volume immediately before can be used or a flow volume calculated by estimate can be used.

It is preferred that the flow volume measurement device 10 calculate the flow volume of the flue gas A also based on the flow volume of the purge gas G flowing in the incident tube 22. Specifically, it is preferred to measure the relation between the magnitude of noise and the flow volume of the flue gas A described above for each flow volume of the purge gas G, to store the measured relation, measure the flow volume of the purge gas G flowing in the incident tube 22, and to select the relation between the magnitude of noise and the flow volume of flue gas to be used based on the measurement result.

A method of calculating the flow volume of the flue gas A also based on the flow volume of the purge gas G is explained below with reference to FIG. 8. FIG. 8 is a graph of a relation between a frequency and noise. In FIG. 8, a vertical axis represents noise (decibels) and a horizontal axis represents a frequency (kilohertz). The frequency indicates a frequency used for demodulating the light reception signal detected by the light receiving unit 44. In FIG. 8, measurement results of the relation between a frequency and noise are shown for cases of the purge flow volume being 1 l/min, 5 l/min, and 10 l/min. The measurement was performed under the same conditions except for the purge flow volume. As shown in FIG. 8, when the purge flow volume is changed, the relation between a frequency and noise also changes. That is, even if demodulation is performed by the same frequency, if the purge flow volume is changed, the magnitude of noise also changes.

Meanwhile, by calculating the flow volume of the flue gas A also based on the flow volume of the purge gas G flowing in the incident tube 22, the flow volume of the flue gas A can be measured with high accuracy. That is, it can be suppressed that the measurement result of the flow volume of the flue gas A has an error due to the change in the purge flow volume. In the case of a configuration in which the purge flow volume is not changed, measurement can be performed with high accuracy, even if the relation between the magnitude of noise to be used and the flow volume of the flue gas A is not changed over according to the flow volume of the purge gas G.

In the above explanations, the relation between the magnitude of noise to be used and the flow volume of flue gas is selected according to the purge flow volume; however, the present invention is not limited thereto. For example, the purge flow volume can be adjusted so that noise to be detected is in a predetermined range. That is, the purge flow volume can be positively adjusted so that noise is in a range in which measurement can be performed easily. For example, when the flow volume of flue gas is small (a low flow volume), the purge flow volume can be increased to increase the measurement sensitivity. When the flow volume of flue gas is large (a high flow volume), the purge flow volume can be decreased to increase the measurement sensitivity.

In the flow volume measurement device 10, the flow-direction detection means 18 that detects the pressure of flue gas in the flow direction thereof to calculate the flow direction of flue gas based on a pressure difference is used; however, the present invention is not limited thereto. Another example of the flow-direction detection means is explained below with reference to FIGS. 9A and 9B, and FIGS. 10 to 13.

Figure 9A:
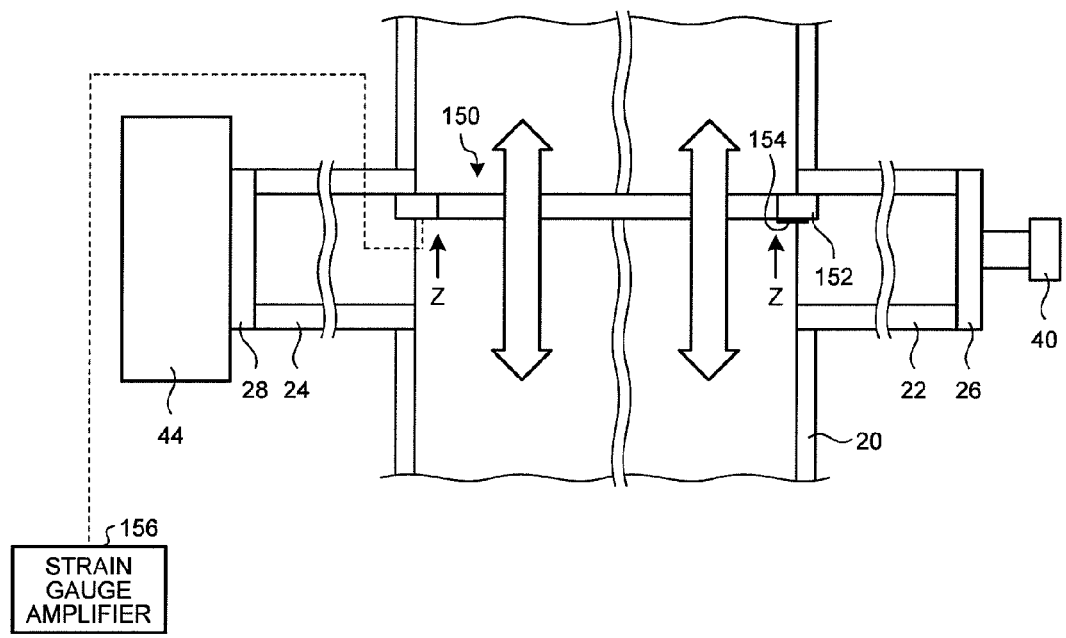
FIG. 9A is a pattern diagram of a schematic configuration of another example of the flow-direction detection means.
Figure 9B:
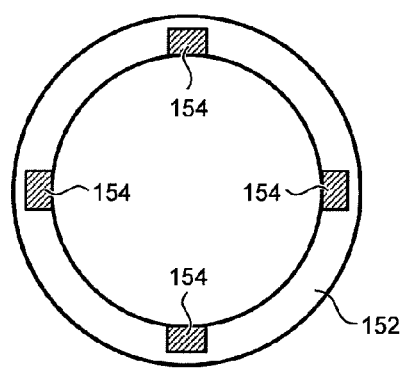
FIG. 9B is a pattern diagram of the flow-direction detection means as viewed from a Z direction in FIG. 9A.

First, another example of the flow-direction detection means is explained with reference to FIGS. 9A and 9B. FIG. 9A is a pattern diagram of a schematic configuration of another example of the flow-direction detection means, and FIG. 9B is a pattern diagram of the flow-direction detection means as viewed from a Z direction in FIG. 9A. A flow-direction detection means 150 shown in FIG. 9A includes a thin-film ring 152, four strain gauges 154, and a strain gauge amplifier 156. The thin-film ring 152 is a circular ring having an outer diameter larger than an inner diameter of the main pipe 20, that is, a ring-shaped member, and one surface thereof is connected to inner surfaces of the incident tube 22 and the emission tube 24, and the main pipe 20. A part of the thin-film ring 152 on an inner diameter side is smaller than the inner diameter of the main pipe 20 and a part thereof is exposed to the inner diameter side of the main pipe 20. The thin-film ring 152 is a thin plate-like member, and is deformed (bent) due to flow of flue gas in the main pipe 20.

The strain gauge (distortion gauge) 154 is arranged, as shown in FIG. 9B, on the surface of the thin-film ring 152, and is deformed together with the thin-film ring 152, thereby detecting deformation of the thin-film ring 152. The strain gauge 154 detects the deformation by a change in electric resistance. In the present embodiment, the strain gauge 154 is provided at four positions; however, the number and an arrangement position of the strain gauge 154 are not particularly limited. The strain gauge 154 transmits the detected deformation to the strain gauge amplifier 156 as an electric signal.

The strain gauge amplifier 156 amplifies the electric signal transmitted from the strain gauge 154 and detects the electric signal as a detection value. Furthermore, the strain gauge amplifier 156 detects a deforming direction of the thin-film ring 152 from the detection value of the strain gauge 154. That is, the strain gauge amplifier 156 detects whether the thin-film ring 152 is deformed in a direction from the outlet of the pipe 8 toward the flue-gas generation device or in a direction from the flue-gas generation device toward the outlet of the pipe 8. After having detected the deforming direction of the strain gauge 154 and the thin-film ring 152, the strain gauge amplifier 156 detects the flow direction of flue gas based on the detected direction. Specifically, when the thin-film ring 152 is deformed in the direction from the outlet of the pipe 8 toward the flue-gas generation device, the strain gauge amplifier 156 detects that flue gas is flowing in the direction from the outlet of the pipe 8 toward the flue-gas generation device. When the thin-film ring 152 is deformed in the direction from the flue-gas generation device toward the outlet of the pipe 8, the strain gauge amplifier 156 detects that flue gas is flowing in the direction from the flue-gas generation device toward the outlet of the pipe 8.

In this manner, the flow direction of flue gas can be detected also by a configuration in which the flow-direction detection means 150 includes a member (the thin-film ring 152) that is deformed into a region of the main pipe 20 where flue gas is flowing and the strain gauge 154 that detects the deformation of the deforming member and a deforming direction thereof. Because the flow direction of flue gas can be detected, the flow and the flow volume of flue gas in the main pipe 20 can be calculated more appropriately.

In the embodiment described above, the thin-film ring 152 is provided on the whole circumference in the circumferential direction; however, the present invention is not limited thereto. For example, a region corresponding to the incident tube 22 and the emission tube 24 can be a notch. Furthermore, the member deformed due to the flow of flue gas is not limited to a ring shape such as the thin-film ring 152. For example, the member deformed due to the flow of flue gas can have a shape protruding from the main pipe 20 only at a measurement position at which the strain gauge 154 is arranged. In this manner, by reducing the portion protruding into the main pipe 20, the influence of the flow-direction detection means 150 on the flow of flue gas can be further reduced.

Figure 10:
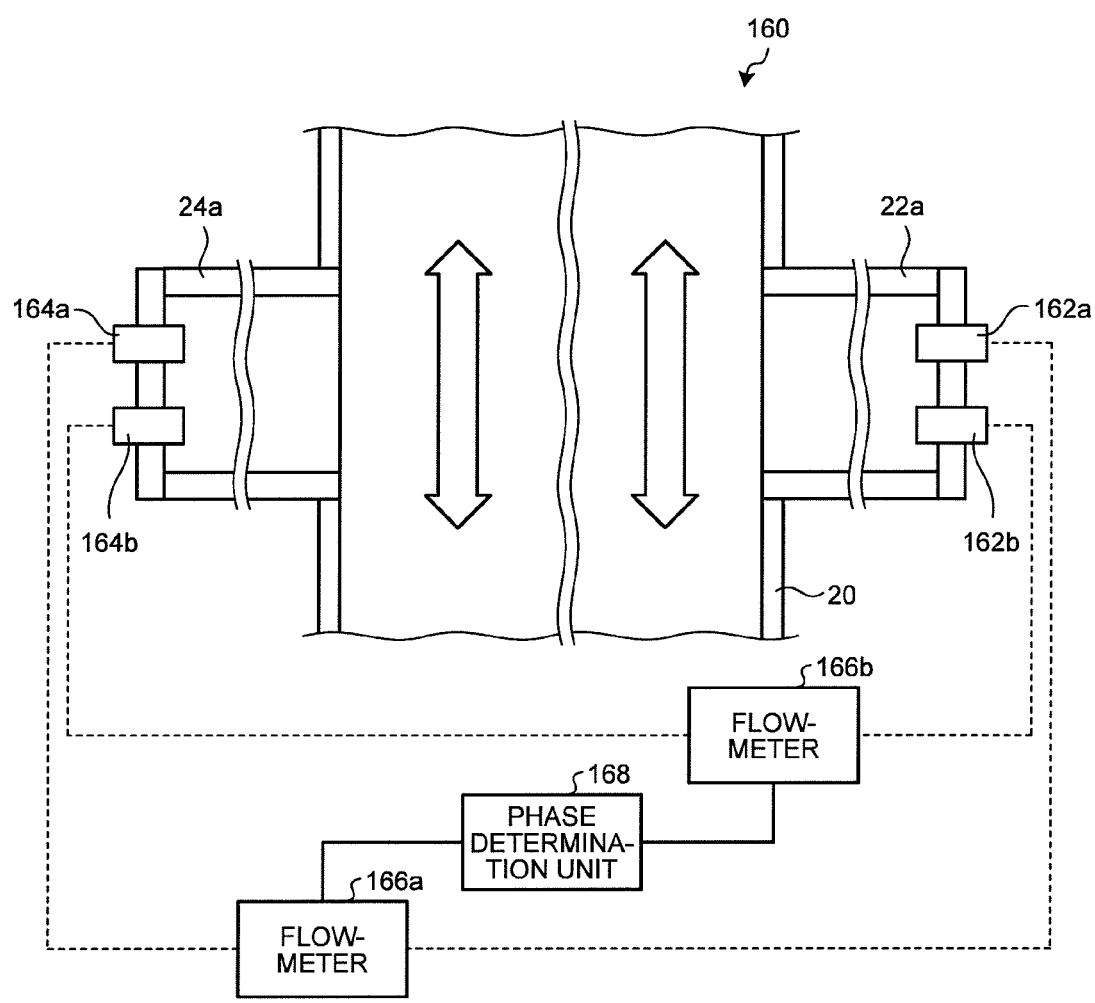
FIG. 10 is a pattern diagram of a schematic configuration of another example of the flow-direction detection means.

Another example of the flow-direction detection means is explained next with reference to FIG. 10. FIG. 10 is a pattern diagram of a schematic configuration of another example of the flow-direction detection means. In FIG. 10, a partial configuration of the measurement means 14 is shown in a simplified manner. A flow-direction detection means 160 shown in FIG. 10 includes two light emitting units 162a and 162b arranged in an incident tube 22a, two light receiving units 164a and 164b arranged in an emission tube 24a, two flowmeters 166a and 166b, and a phase determination unit 168.

The light emitting unit 162a is arranged on a side closer to the flue-gas generation device than the light emitting unit 162b in the flow direction of flue gas. The light receiving unit 164a is also arranged on the side closer to the flue-gas generation device than the light receiving unit 164b in the flow direction of flue gas. That is, the light emitting unit 162a and the light receiving unit 164a are arranged on the side closer to the flue-gas generation device than the light emitting unit 162b and the light receiving unit 164b, and the light emitting unit 162b and the light receiving unit 164b are arranged on the outlet side of the pipe 8 than the light emitting unit 162a and the light receiving unit 164a. Light emitted from the light emitting unit 162a passes through the main pipe 20 and enters into the light receiving unit 164a. Light emitted from the light emitting unit 162b passes through the main pipe 20 and enters into the light receiving unit 164b.

The flowmeter 166a measures a flow volume of flue gas flowing in the main pipe 20 based on a relation between light emitted from the light emitting unit 162a and light received by the light receiving unit 164a. The flowmeter 166b measures the flow volume of flue gas flowing in the main pipe 20 based on a relation between light emitted from the light emitting unit 162b and light received by the light receiving unit 164b. In this manner, the light emitting unit 162a, the light receiving unit 164a, and the flowmeter 166a forms one measurement means, and the light emitting unit 162b, the light receiving unit 164b, and the flowmeter 166b forms one measurement means as well. That is, the flow-direction detection means 160 includes two measurement means, and the respective measurement means measure the flow volume of gas.

The phase determination unit 168 determines a flow direction of flue gas based on a change in the flow volume calculated by the flowmeter 166a and a change in the flow volume calculated by the flowmeter 166b. Specifically, the light emitting unit 162a, the light receiving unit 164a, and the flowmeter 166a and the light emitting unit 162b, the light receiving unit 164b, and the flowmeter 166b respectively measure the flow volume of flue gas at different positions in the flow direction of flue gas. Therefore, when there is a change in the flow volume, certain time delay occurs. That is, a phase difference occurs in the flow volume to be measured. The phase determination unit 168 calculates the flow direction of flue gas based on the phase difference in the flow volume. Specifically, when there is a phase delay in the flow volume measured by the flowmeter 166a with respect to the flow volume measured by the flowmeter 166b, the phase determination unit 168 determines that flue gas flows from the outlet of the pipe 8 toward the flue-gas generation device. When there is a phase delay in the flow volume measured by the flowmeter 166b with respect to the flow volume measured by the flowmeter 166a, the phase determination unit 168 determines that flue gas flows from the flue-gas generation device toward the outlet of the pipe 8.

In this manner, when a plurality of means that measure the flow volume of flue gas are provided and arranged at different positions in the flow direction of flue gas, the flow direction of flue gas can be detected based on time delay of measurement values thereof. Because the flow direction of flue gas can be detected based on the flow volume of flue gas, the flow direction of flue gas can be detected only by providing a computing function without adding another configuration.

The flow volume detection means of flue gas can measure the concentration of a specific substance contained in flue gas as well, as described above.

Figure 11:
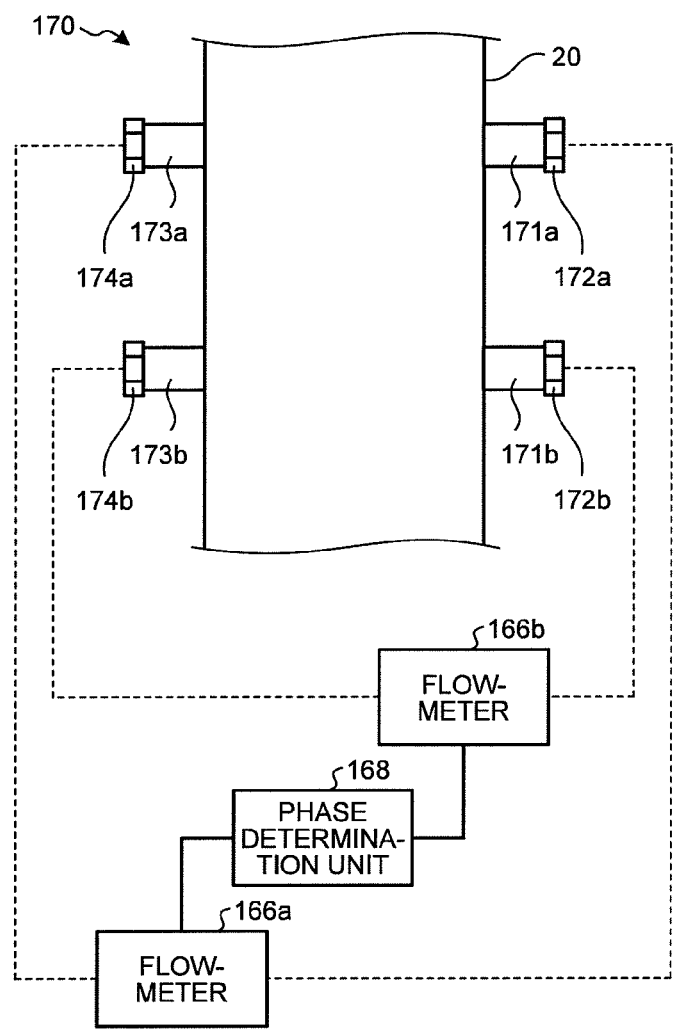
FIG. 11 is a pattern diagram of a schematic configuration of another example of the flow-direction detection means.

In the example shown in FIG. 10, the two light emitting units 162a and 162b are provided in one incident tube 22a, and the two light receiving units 164a and 164b are provided in one emission tube 24a. However, these can be provided in an individual tube. This is explained with reference to FIG. 11. FIG. 11 is a pattern diagram of a schematic configuration of another example of the flow-direction detection means. A flow-direction detection means 170 shown in FIG. 11 includes a light emitting unit 172a arranged in an incident tube 171a, a light emitting unit 172b arranged in an incident tube 171b, a light receiving unit 174a arranged in an emission tube 173a, a light receiving unit 174b arranged in an emission tube 173b, two flowmeters 166a and 166b, and the phase determination unit 168. The flowmeters 166a and 166b and the phase determination unit 168 respectively have the same configuration as those shown in FIG. 10.

The incident tube 171a and the emission tube 173a are respectively in a cylindrical shape, and arranged at a position where axes of two cylinders overlap on each other. Therefore, light emitted from the light emitting unit 172a arranged in the incident tube 171a passes through the main pipe 20, and enters into the light receiving unit 174a arranged in the emission tube 173a. Furthermore, the incident tube 171b and the emission tube 173b are also respectively in a cylindrical shape, and arranged at a position where axes of two cylinders overlap on each other. Therefore, light emitted from the light emitting unit 172b arranged in the incident tube 171b passes through the main pipe 20, and enters into the light receiving unit 174b arranged in the emission tube 173b. The incident tube 171a, the light emitting unit 172a, the emission tube 173a, and the light receiving unit 174a are arranged closer to the flue-gas generation device than the incident tube 171b, the light emitting unit 172b, the emission tube 173b, and the light receiving unit 174b.

As in the flow-direction detection means 170, even if the measurement means that measures the flow volume is separately provided, the flow direction of flue gas can be calculated by the same method as that of the flow-direction detection means 160. In the flow-direction detection means 170 shown in FIG. 11, the means that measures the flow volume (a traveling direction of measuring beam) is arranged in a direction orthogonal to the flow direction of flue gas. However, the measurement means can be provided to be inclined by a predetermined angle.

Figure 12:
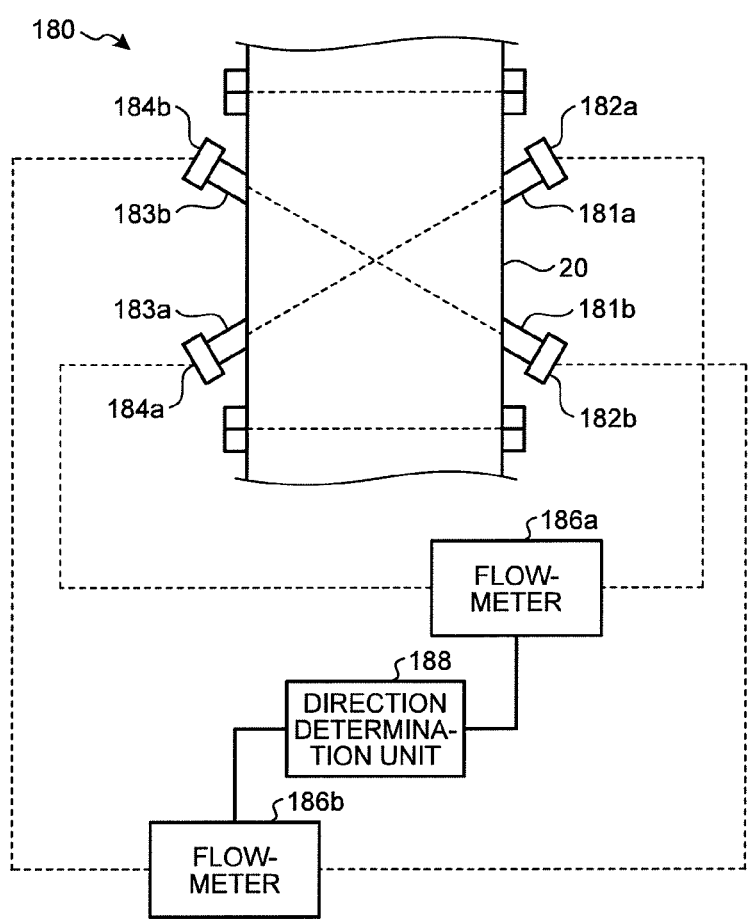
FIG. 12 is a pattern diagram of a schematic configuration of another example of the flow-direction detection means.

In the flow-direction detection means shown in FIG. 10 or FIG. 11, the means that measures the flow volume (the traveling direction of measuring beam) is arranged in parallel. However, the present invention is not limited thereto. Another example is explained with reference to FIG. 12. FIG. 12 is a pattern diagram of a schematic configuration of another example of the flow-direction detection means.

A flow-direction detection means 180 shown in FIG. 12 includes a light emitting unit 182a arranged in an incident tube 181a, a light emitting unit 182b arranged in an incident tube 181b, a light receiving unit 184a arranged in an emission tube 183a, a light receiving unit 184b arranged in an emission tube 183b, two flowmeters 186a and 186b, and a direction determination unit 188.

The incident tube 181a and the emission tube 183a are respectively in a cylindrical shape, and arranged at a position where axes of two cylinders overlap on each other. Therefore, light emitted from the light emitting unit 182a arranged in the incident tube 181a passes through the main pipe 20, and enters into the light receiving unit 184a arranged in the emission tube 183a. Furthermore, the incident tube 181b and the emission tube 183b are also respectively in a cylindrical shape, and arranged at a position where axes of two cylinders overlap on each other. Therefore, light emitted from the light emitting unit 182b arranged in the incident tube 181b passes through the main pipe 20, and enters into the light receiving unit 184b arranged in the emission tube 183b.

In the present embodiment, the incident tube 181a is arranged closer to the flue-gas generation device than the incident tube 181b, and the emission tube 183a is arranged closer to the outlet of the pipe 8 than the emission tube 183b. A traveling direction of light output from the light emitting units 182a and 182b is inclined by a predetermined angle with respect to a direction orthogonal to a flow direction of flue gas. Specifically, light output from the light emitting unit 182a is emitted in a direction inclined toward the outlet of the pipe 8 with respect to the direction orthogonal to the flow direction of flue gas. Light output from the light emitting unit 182b is emitted in a direction inclined toward the flue-gas generation device with respect to the direction orthogonal to the flow direction of flue gas. A path from the light emitting unit 182a to the light receiving unit 184a and a path from the light emitting unit 182b to the light receiving unit 184b have substantially the same length.

The flowmeter 186a measures a flow volume of flue gas flowing in the main pipe 20 based on a relation between light emitted from the light emitting unit 182a and light received by the light receiving unit 184a. The flowmeter 186b measures the flow volume of flue gas flowing in the main pipe 20 based on a relation between light emitted from the light emitting unit 182b and light received by the light receiving unit 184b.

The direction determination unit 188 detects the flow direction of flue gas based on the flow volumes respectively detected by the flowmeters 186a and 186b. Specifically, in the flow-direction detection unit 180, the flow volume measured by any one of the flowmeter 186a and the flowmeter 186b increases according to the flow direction of flue gas. It can be considered this is because a temperature boundary layer to be formed is changed due to a different angle formed between the incident tubes 181a and 181b and the main pipe 20. The direction determination unit 188 determines the difference in these detection values and which detection value is larger and detects the flow direction of flue gas based on the determination result.

Also by using the configuration of the flow-direction detection means 180, the flow direction of flue gas can be detected more appropriately. In addition, it can be also determined which of the units of the measurement means can detect the flow volume of flue gas more appropriately.

Figure 13:
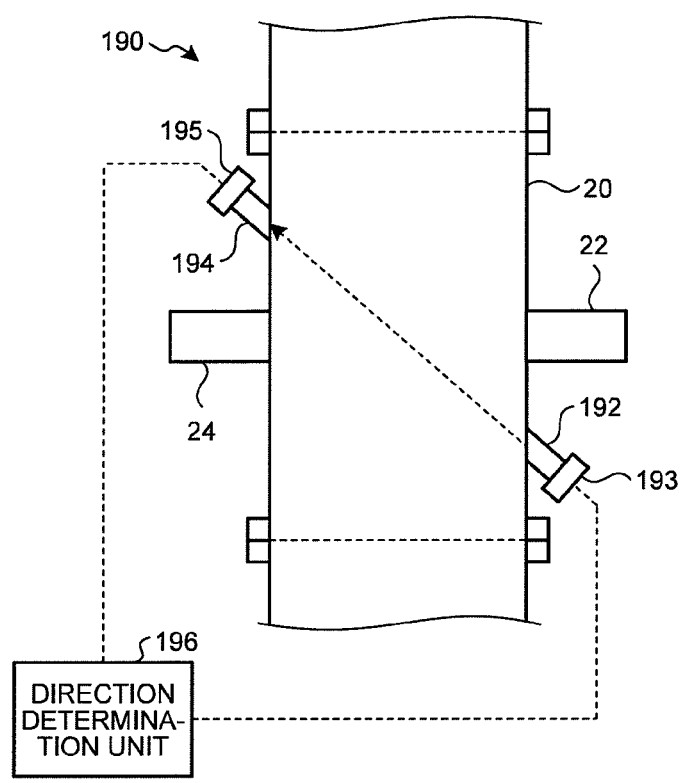
FIG. 13 is a pattern diagram of a schematic configuration of another example of the flow-direction detection means.

Another example of the flow-direction detection means is explained next with reference to FIG. 13. FIG. 13 is a pattern diagram of a schematic configuration of another example of the flow-direction detection means. A flow-direction detection means 190 detects a flow direction of flue gas by using an ultrasonic wave, and includes an incident tube 192, a transmission unit 193, an emission tube 194, a reception unit 195, and a direction determination unit 196.

The incident tube 192 and the emission tube 194 are respectively in a cylindrical shape, and arranged at a position where axes of two cylinders overlap on each other. The incident tube 192 is arranged on a side closer to the outlet of the pipe 8 than the emission tube 194. That is, the incident tube 192 and the emission tube 194 are inclined by a predetermined angle with respect to a direction orthogonal to a flow direction of flue gas.

The transmission unit 193 is a transmitter that outputs ultrasonic waves, and outputs the ultrasonic wave from the incident tube 192 toward the main pipe 20. The reception unit 195 is arranged in the emission tube 194, and receives the ultrasonic wave output from the transmission unit 193, having passed through the incident tube 192 and the main pipe 20, and having reached the emission tube 194. A traveling direction of the ultrasonic wave is inclined by a predetermined angle with respect to the direction orthogonal to the flow of flue gas. Specifically, light output from the transmission unit 193 is emitted in a direction inclined toward the flue-gas generation device with respect to the direction orthogonal to the flow of flue gas.

The direction determination unit 196 detects the flow direction of flue gas based on a frequency (a wavelength) of the ultrasonic wave transmitted by the transmission unit 193 and a frequency (a wavelength) of the ultrasonic wave received by the reception unit 195. Specifically, when having determined that a frequency of the ultrasonic wave becomes larger (the wavelength becomes shorter) than a reference value, the direction determination unit 196 determines that flue gas is flowing from the flue-gas generation device toward the outlet of the pipe 8. When having determined that the frequency of the ultrasonic wave becomes smaller (the wavelength becomes longer) than the reference value, the direction determination unit 196 determines that flue gas is flowing from the outlet of the pipe 8 toward the flue-gas generation device.

The flow direction of flue gas can be detected by using the ultrasonic wave as in the flow-direction detection means 190.

The means that detects the flow direction of flue gas is not limited to the means described in the above embodiments, and various methods can be used.

Figure 14A:
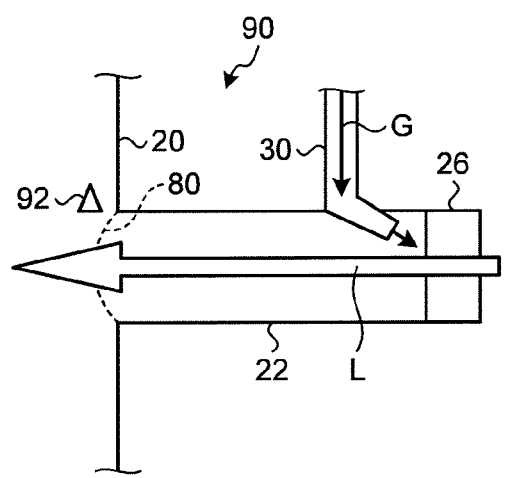
FIG. 14A is a pattern diagram of a partial schematic configuration of a flow volume measurement device according to another embodiment.
Figure 14B:
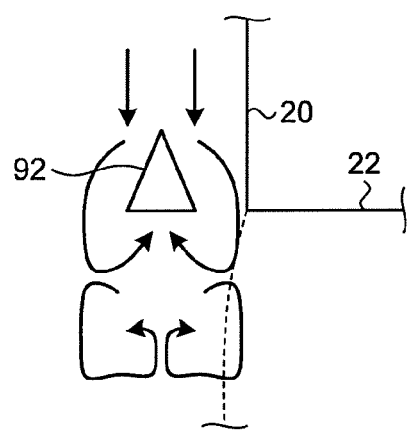
FIG. 14B is a partially enlarged diagram of FIG. 14A.

It is preferred that a turbulence generation unit that generates turbulence in the periphery of the temperature boundary layer is provided in the flow volume measurement device 10. This configuration is explained below with reference to FIGS. 14A and 14B. FIG. 14A is a pattern diagram of a partial schematic configuration of a flow volume measurement device according to another embodiment, and FIG. 14B is a partially enlarged diagram of FIG. 14A.

A measurement cell 90 shown in FIG. 14A includes a protrusion 92, which becomes the turbulence generation unit. The protrusion 92 is arranged in an upstream of the incident tube 22 in a flow direction of flue gas in the main pipe 20 and near the incident tube 22, that is, near a connection part between the main pipe 20 and the incident tube 22. The protrusion 92 is protruding to the upstream side of the flue gas flow, and generates turbulence in the downstream of the protrusion 92 as shown in FIG. 14B.

By providing the protrusion 92 as the turbulence generation unit as described above, turbulence (such as Karman vortex) can be generated in a passage route of the laser beam, and turbulence begins from the temperature boundary layer, thereby enabling to further increase noise. Noise can be easily measured by increasing noise, thereby enabling to further increase the measurement sensitivity. Because noise can be easily measured, the flow volume can be easily calculated. Because noise as a detection value increases, measurement can be performed with higher sensitivity. That is, by providing the turbulence generation unit, a change in the magnitude of noise (a characteristic of a light reception signal) with respect to a change in the flow volume of flue gas can be further increased. Accordingly, the flow volume can be measured highly accurately.

The flow volume measurement device 10 can measure the concentration of a specific substance contained in flue gas in addition to the flow volume of flue gas. The flow volume measurement device 10 can measure the concentration by performing calculation by the calculation unit based on a detection value, basically, without providing a new device.

First, at the time of measuring the concentration, the light emitting unit 40 is a light emitting element that emits a laser beam in a near-infrared wavelength region absorbed by a substance to be measured. For example, when the substance to be measured is nitrogen monoxide, the light emitting unit 40 includes a light emitting element that emits a laser beam in the near-infrared wavelength region for absorbing nitrogen monoxide. When the substance to be measured is nitrogen dioxide, the light emitting unit 40 includes a light emitting element that emits a laser beam in the near-infrared wavelength region for absorbing nitrogen dioxide. When the substance to be measured is nitrous oxide, the light emitting unit 40 includes a light emitting element that emits a laser beam in the near-infrared wavelength region for absorbing nitrous oxide. When a plurality of substances are to be measured, the light emitting unit 40 can include a plurality of light emitting elements that respectively emit light in a wavelength region absorbed by each substance. The light source driver 46 and the control unit 50 output intensity information of the laser beam being output from the light emitting unit 40 to the calculation unit 48.

The calculation unit 48 calculates the concentration of the substance to be measured based on a signal (a light reception signal) transmitted from the light receiving unit 44 and a condition for driving the light source driver 46 by the control unit 50. Specifically, the calculation unit 48 calculates an intensity of the laser beam output from the light emitting unit 40 based on the condition for driving the light source driver 46 by the control unit 50, and calculates the intensity of the received laser beam based on the light reception signal transmitted from the light receiving unit 44. The calculation unit 48 compares the intensity of the emitted laser beam with the intensity of the received laser beam to calculate the concentration of the substance to be measured contained in the flue gas A.

Specifically, the laser beam L in the near-infrared wavelength region output from the light emitting unit 40 reaches the light receiving unit 44 after having passed through a predetermined route of the measurement cell 12 from the optical fiber 42, more specifically, through the window 26, the incident tube 22, the main pipe 20, the emission tube 24, and the window 28. At this time, when the flue gas A in the measurement cell 12 contains the substance to be measured, the laser beam passing through the measurement cell 12 is absorbed. Therefore, an output of the laser beam L reaching the light receiving unit 44 changes according to the concentration of the substance to be measured in the flue gas A. The light receiving unit 44 converts the received laser beam to a light reception signal and outputs the light reception signal to the calculation unit 48. Furthermore, the control unit 50 and the light source driver 46 output the intensity of the laser beam L output from the light emitting unit 40 to the calculation unit 48. The calculation unit 48 compares the intensity of light output from the light emitting unit 40 with the intensity calculated based on the light reception signal to calculate the concentration of the substance to be measured in the flue gas A flowing in the measurement cell 12 based on a reduced rate. In this manner, the measurement means 14 can either calculate or measure the concentration of the substance to be measured in the flue gas A passing through a predetermined position, that is, a measurement position in the main pipe 20 based on the intensity of the output laser beam and the light reception signal detected by the light receiving unit 44, by using a so-called TDLAS method (Tunable Diode Laser Absorption Spectroscopy). The measurement means 14 can either calculate or measure the concentration of the substance to be measured continuously.

At the time of measuring the concentration of a specific substance contained in gas as well, the flow volume measurement device 10 can measure the concentration of various substances by adjusting the device, more specifically, by adjusting a wavelength of the laser beam to be output. As the various substances to be measured, nitrogen oxide, sulfur oxide, carbon monoxide, carbon dioxide, ammonia and the like are exemplified.

In this manner, the flow volume measurement device 10 can measure the flow volume of flue gas and the concentration of a specific substance in flue gas simultaneously, basically without increasing the device configuration. In the above embodiment, because only a desired substance can be selected and measured highly accurately, the concentration is measured by the TDLAS method. However, the present invention is not limited thereto, and various methods of measuring the concentration by receiving the laser beam having passed through the main pipe can be used.

Figure 15A:
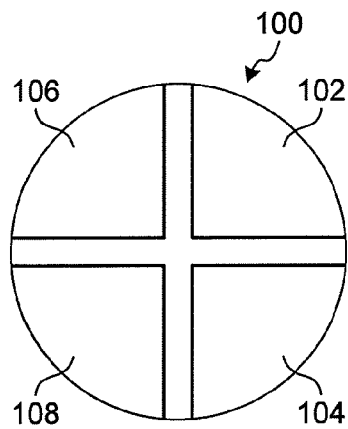
FIG. 15A is a pattern diagram of a schematic configuration of a light receiving unit of the flow volume measurement device according to another embodiment.
Figure 15B:
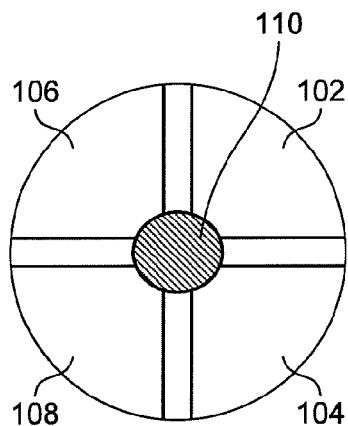
FIG. 15B is an explanatory diagram for explaining an operation of the flow volume measurement device shown in FIG. 15A.
Figure 15C:
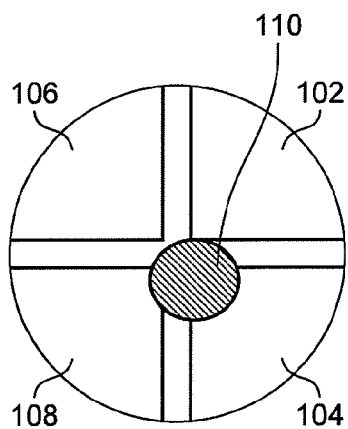
FIG. 15C is an explanatory diagram for explaining an operation of the flow volume measurement device shown in FIG. 15A.

A flow volume measurement device according to another embodiment is explained next with reference to FIGS. 15A to 15C. FIG. 15A is a pattern diagram of a schematic configuration of a light receiving unit of the flow volume measurement device according to another embodiment. FIGS. 15B and 15C are explanatory diagrams of an operation of the flow volume measurement device shown in FIG. 15A. Other configurations of the flow volume measurement device having the light receiving unit shown in FIG. 15A are the same as those of the flow volume measurement device 10, except for the shape of the light receiving unit.

A light receiving unit 100 shown in FIG. 15A includes four light receiving elements 102, 104, 106, and 108. Each of the light receiving elements 102, 104, 106, and 108 is a photodetector such as a photodiode (PD) and transmits the intensity (an amount of light) of the received laser beam to the calculation unit 48 as a light reception signal. The four light receiving elements 102, 104, 106, and 108 have the same shape, and are arranged adjacent to each other. Specifically, the light receiving element 102 abuts on the light receiving element 104 on one side and abuts on the light receiving element 106 on the other side contacting the one side. The light receiving element 104 abuts on the light receiving element 102 on one side and abuts on the light receiving element 108 on the other side contacting the one side. The light receiving element 106 abuts on the light receiving element 102 on one side and abuts on the light receiving element 108 on the other side contacting the one side. The light receiving element 108 abuts on the light receiving element 106 on one side and abuts on the light receiving element 104 on the other side contacting the one side. That is, when it is assumed that the light receiving unit 100 is an xy plane in which a center thereof is designated as an origin, and a side at the boundary of respective elements is designated as an x-axis and a y-axis, respectively, the light receiving element 102 is arranged in a first quadrant, the light receiving element 106 is arranged in a second quadrant, the light receiving element 108 is arranged in a third quadrant, and the light receiving element 104 is arranged in a fourth quadrant.

For example, if the laser beam is not refracted at the time of passing through the temperature boundary layer, as shown in FIG. 15B, a laser beam 110 reaches the origin described above, and light reaches evenly to the four light receiving elements 102, 104, 106, and 108. On the other hand, if the laser beam 110 is refracted at the time of passing through the temperature boundary layer, for example, as shown in FIG. 15C, a reached position of the laser beam 110 moves toward the light receiving element 104, and the light receiving element 106 does not receive the laser beam. Therefore, in the light receiving unit 100, when the reached position is shifted, light received by the respective light receiving elements increases or decreases, and the light reception signal undergoes a change. Furthermore, although an amount of light received by each light receiving element fluctuates, a sum total of the reached laser beam 110 can be calculated by summing up the intensity of light received by the four light receiving elements 102, 104, 106, and 108.

With this configuration, the flow volume measurement device including the light receiving unit 100 can calculate the flow volume of flue gas from noise in the light reception signal received by one light receiving element. The flow volume measurement device can measure the concentration of flue gas to be measured, based on the sum total of the light reception signals received by the four light receiving elements. Accordingly, even if the reached position of the laser beam has changed, the flow volume measurement device can receive all the reached light and measure the concentration of a measurement object based on the received light intensity, thereby enabling to measure the concentration of the measurement object highly accurately.

In the above embodiment, the flow volume is calculated by the method described above, based on noise in the light reception signal detected by one light receiving element. However the present invention is not limited thereto. For example, the flow volume can be calculated by comparing light reception amounts of the respective light receiving elements with each other. That is, a relative change in the four light receiving elements 102, 104, 106, and 108 can be calculated as a noise. Specifically, a perturbation, a fluctuation, and a shift amount of the laser beam are calculated based on an increase or decrease in the light reception amount, and the flow volume can be calculated based on a calculation result thereof.

For example, when a relationship between a purge flow volume and a flow volume of flue gas changes, a shape of the temperature boundary layer also changes. Accordingly, a fluctuation speed and a maximum moving distance from the origin of the fluctuation frequency of the laser beam also change. The calculation unit 48 stores therein these relations calculated by experiments or the like in advance, and calculates the flow volume based on calculation results (a ratio in the light reception amount by the respective light receiving elements, a changed frequency and the like) and the stored relations, based on the light reception signal.

Furthermore, the calculation unit 48 can calculate the reached position of the laser beam 110 based on the relationship among the four light receiving elements 102, 104, 106, and 108 to calculate the flow volume of flue gas based on the reached position and the origin. That is, the maximum moving distance of the laser beam (an amount of displacement from the origin) can be calculated based on the relationship between the purge flow volume and the flow volume of flue gas. Accordingly, the flow volume of flue gas can be calculated also by calculating the moving distance of the laser beam.

Figure 16:
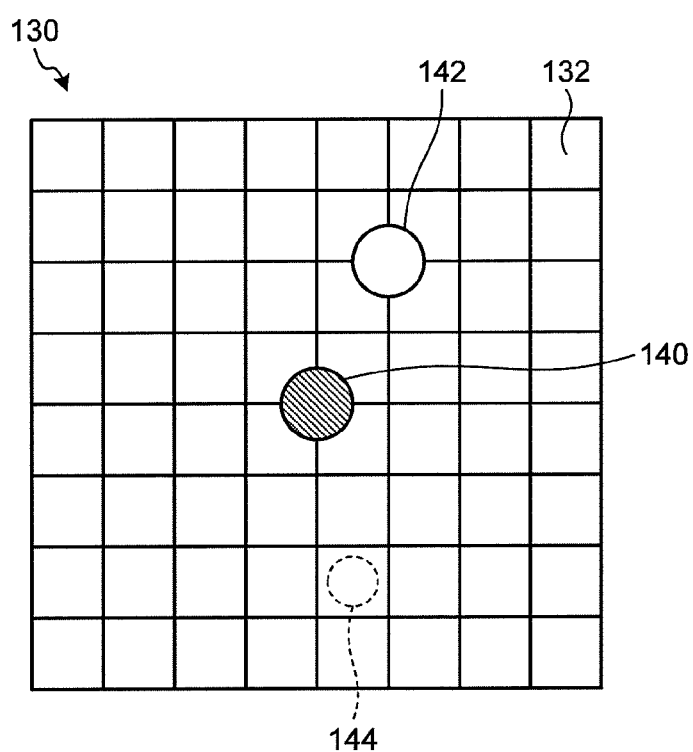
FIG. 16 is a pattern diagram of a schematic configuration of another example of the light receiving unit.

In the above embodiment, the reached position of the laser beam is calculated based on a balance in the light reception amounts of the four light receiving elements; however, the present invention is not limited thereto. Another example of the light receiving unit is explained with reference to FIG. 16. FIG. 16 is a pattern diagram of a schematic configuration of another example of the light receiving unit. Light receiving elements 132 are arranged in a matrix in a light receiving unit 130 shown in FIG. 16. Specifically, 64 light receiving elements 132 are arranged vertically and horizontally in a matrix of eight by eight. The 64 light receiving elements 132 of the light receiving unit 130 respectively transmit a light reception signal to the calculation unit 48.

In this manner, the reached position of the laser beam can be calculated based on a position of the light receiving element that has received the laser beam by arranging the light receiving elements in a matrix. For example, when a laser beam 140 has reached the center of the 8×8 matrix, four light receiving elements at the center detect the laser beam. In this case, the center of the four light receiving elements can be set as the reached position. When the laser beam has moved and the reached position of the laser beam has become position 142, the center of the four light receiving elements having received the laser beam can be set as the reached position. When the laser beam has further moved and the reached position of the laser beam has become position 144, the light receiving element that has received the laser beam is only one. In this case, the position of the one light receiving element can be set as the reached position.

In this manner, by arranging a plurality of light receiving elements in a matrix, the reached position of the laser beam can be detected without detecting a balance in the light reception amounts. Furthermore, the flow volume measurement device can calculate the flow volume based on information of the reached position. An arrangement sequence of the light receiving elements is not limited to the present embodiment. For example, the light receiving elements can be arranged densely in the central part and arranged sparsely as moving away from the center.

The flow volume measurement device is not limited to the above embodiment. The flow volume measurement device can use a fact that a characteristic of fluctuation in the reached position of the laser beam changes according to the relationship between the flow volume of flue gas and the flow volume of purge gas, and can use various methods of calculating the flow volume of flue gas based on the light reception signal from the light receiving unit. That is, the flow volume measurement device of the present invention calculates the flow volume of flue gas by calculating various characteristics (noise, fluctuation position, and moving distance) of fluctuations in the reached position of the laser beam based on the light reception signal transmitted from the light receiving unit, and also by taking the flow volume of purge gas into consideration as required.

As described above, purge gas can be efficiently supplied to the periphery of the windows 26 and 28 by arranging the outlets of the purge-gas supply pipes 30 and 32 toward the windows 26 and 28, thereby enabling to reliably prevent the windows 26 and 29 from being contaminated. Therefore, it is preferred that the outlets of the purge-gas supply pipes 30 and 32 be arranged toward the windows 26 and 28. However, the present invention is not limited thereto. For example, purge gas can be discharged in a direction vertical to the axes of the incident tube and the emission tube.

In the above embodiment, the incident tube and the emission tube are provided coaxially; however, the present invention is not limited thereto. For example, an optical mirror can be provided in the measurement cell, and after the laser beam entering from the window of the incident tube is multiply-reflected by the optical mirror in the measurement cell, the laser beam can reach the window of the emission tube. In this manner, the laser beam can pass through more areas in the measurement cell by being multiply-reflected. Accordingly, an influence of concentration distribution of flue gas flowing in the measurement cell (a difference in the flow volume or density of flue gas, and a difference in concentration distribution in flue gas) can be decreased, and the concentration can be accurately detected.

In the above embodiment, the main pipe of the measurement cell and the pipe for allowing passage of flue gas are different members. However, these can be integrated. For example, the main pipe of the measurement cell can be directly connected to the device that discharges flue gas.

Furthermore, the shape of the main pipe of the measurement cell needs only to allow passage of the laser beam, and the main pipe can have a circular shape in cross-section, a polygonal shape in cross-section, or an elliptical shape in cross-section. Further, a cross-section of an inner periphery of the pipe and a cross-section of an outer periphery of the pipe can have a different shape. The shapes of the incident tube and the emission tube are not particularly limited as described above.

In the above embodiment, the flow volume of gas flowing in the pipe is measured. However, the present invention is not limited thereto, and a flow velocity can be measured as well. For example, the flow velocity can be calculated by using the relation between the light reception signal and the flow volume described above and a relation between the flow volume and the flow velocity. That is, because a diameter of the pipe is constant, the flow velocity can be calculated by dividing the calculated flow volume by the diameter of the pipe. The flow velocity can be calculated based on a measurement value of the light reception signal by calculating the relation in advance such as the relation between the light reception signal and the flow volume. That is, the flow volume measurement device can be used as the flow velocity measurement device by changing the calculation method and a formula for computation by the calculation unit. Furthermore, the flow volume measurement device can also have a flow-velocity measurement function. As described above, even at the time of measuring the flow velocity, measurement can be performed with high responsiveness, and under severe environmental conditions. Even at the time of measuring the flow velocity of flue gas, the flow direction of flue gas can be detected together, thereby enabling to detect flow of flue gas more appropriately.

When the flow velocity is to be measured, the measurement is not limited to the flow velocity of gas (fluid) flowing in the pipe (a flow channel), and measurement can be performed with respect to the flow velocity of fluid flowing in a measurement area, by designating an area between the incident tube and the emission tube (a passage route of the laser beam) as the measurement area. That is, not only the flow velocity of the fluid flowing in a closed flow channel but also the flow velocity of fluid flowing in an open measurement area can be measured.

Figure 17:
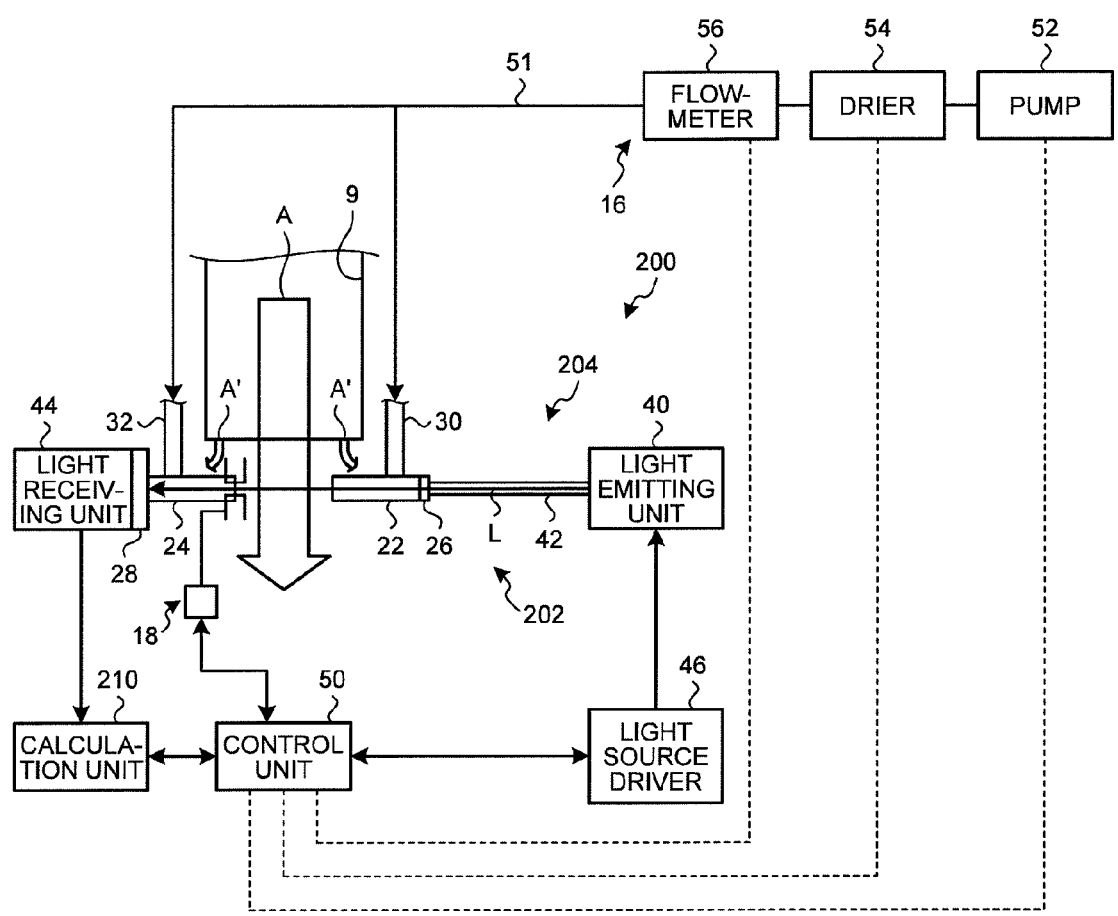
FIG. 17 is a pattern diagram of a schematic configuration of a flow velocity measurement device according to an embodiment of the present invention.
Figure 18A:
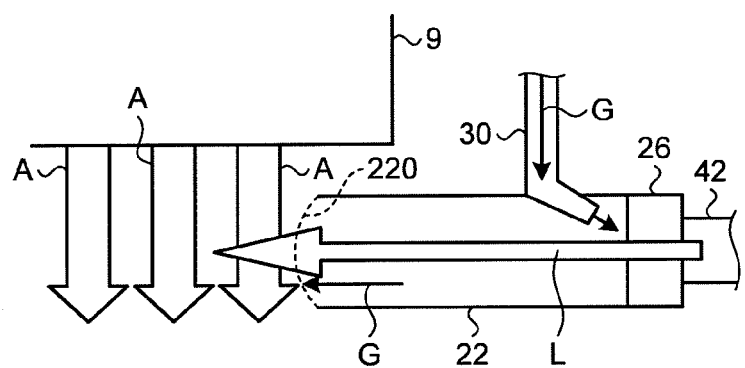
FIG. 18A is an enlarged pattern diagram of a part of a measurement cell of the flow velocity measurement device shown in FIG. 17 in an enlarged manner.
Figure 18B:
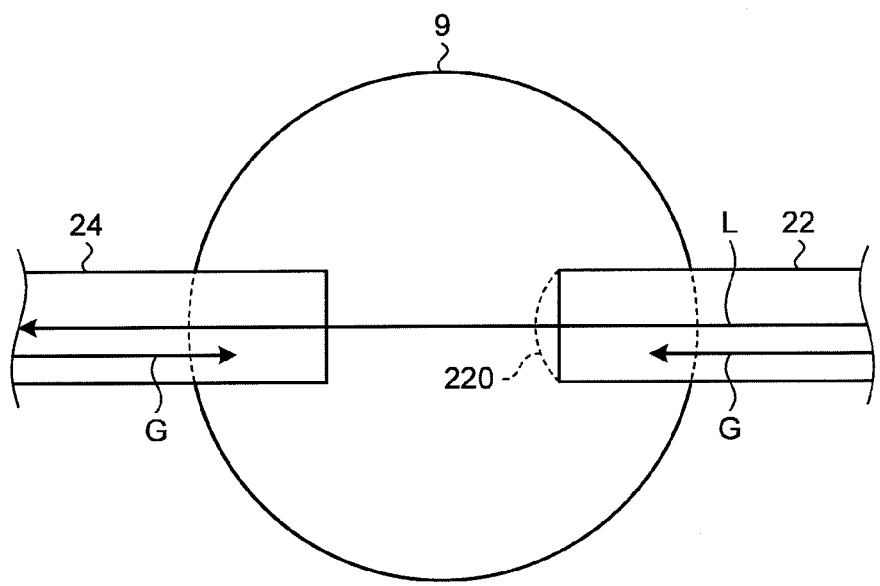
FIG. 18B is a pattern diagram of the measurement cell of the flow velocity measurement device shown in FIG. 17 as viewed from a direction parallel to a flow direction of flue gas.

An example of a flow velocity measurement device is explained below with reference to FIGS. 17, 18A, and 18B. FIG. 17 is a pattern diagram of a schematic configuration of a flow velocity measurement device according to an embodiment of the present invention. FIG. 18A is an enlarged pattern diagram of a part of a measurement cell of the flow velocity measurement device shown in FIG. 17 in an enlarged manner. FIG. 18B is a pattern diagram of the measurement cell of the flow velocity measurement device shown in FIG. 17 as viewed from a direction parallel to the flow direction of flue gas. In a flow velocity measurement device 200, only a relation between a discharge supply device that discharges flue gas and piping thereof, and a calculation method by a calculation unit 210 are different from those of the flow volume measurement device 10, and other configurations of the flow velocity measurement device 200 are the same as those of the flow volume measurement device 10. Therefore, constituent elements identical to those of the flow volume measurement device 10 are denoted by like reference signs and explanations thereof will be omitted, and configurations specific to the flow velocity measurement device 200 are explained below.

As shown in FIG. 17, the flow velocity measurement device 200 includes a measurement cell 202, a measurement means 204, and the purge-gas supply means 16 to measure a flow velocity when the flue gas A discharged from a pipe 9 passes through a predetermined measurement area. A part of flue gas discharged from the pipe 9 passes through the measurement area, and a part of flue gas A' does not pass through the measurement area.

The measurement cell 202 basically includes the incident tube 22 and the emission tube 24. The incident tube 22 is provided with the window 26 and the purge-gas supply pipe 30, and the emission tube 24 is provided with the window 28 and the purge-gas supply pipe 32. That is, the measurement cell 202 has the same configuration as that of the measurement cell 12 except that the main pipe is not provided. Arrangement positions of the incident tube 22 and the emission tube 24 are explained next.

As shown in FIGS. 17, 18A, and 18B, the incident tube 22 is arranged on a downstream side of a terminal end of the pipe 9 and at a position away from the pipe 9 by a certain distance in a discharge direction of the flue gas A. As shown in FIG. 18B, one end of the incident tube 22 (an end from which the purge gas G is discharged) is arranged inside of an area of an aperture plane of the pipe 9 bounded by an extended line.

The emission tube 24 is also arranged on the downstream side of the terminal end of the pipe 9 and at a position away from the pipe 9 by a certain distance in the discharge direction of the flue gas A. As shown in FIG. 18B, one end of the emission tube 24 (an end from which the purge gas G is discharged) is arranged inside of the area of the aperture plane of the pipe 9 bounded by the extended line. The emission tube 24 is arranged opposite to the incident tube 22. Specifically, the emission tube 24 is arranged with the one end facing the one end of the incident tube 22 and at a position where the flue gas A flows between the incident tube 22 and the emission tube 24. The arrangement positions of the incident tube 22 and the emission tube 24 can be fixed by an arbitrarily support unit.

The measurement cell 202 has the above-described configuration, and the laser beam L entering from the window 26 into the incident tube 22 passes through the space between the incident tube 22 and the emission tube 24 (the measurement area). The laser beam L having passed through the measurement area passes through the emission tube 24 and the window 28, and is received by the light receiving unit 44.

The measurement means 204 includes the light emitting unit 40, the optical fiber 42, the light receiving unit 44, the light source driver 46, the calculation unit 210, and the control unit 50. Because the light emitting unit 40, the optical fiber 42, the light receiving unit 44, the light source driver 46, and the control unit 50 are the same as the respective units of the measurement means 14 described above, explanation thereof is omitted.

The calculation unit 210 stores therein the relation between the light reception signal and the flow velocity in advance, and calculates the flow velocity of the flue gas A flowing in the measurement area based on the light reception signal transmitted from the light receiving unit 44. The calculation of the flow velocity is explained later.

The flow velocity measurement device 200 supplies the purge gas G to the incident tube 22 and the emission tube 24 by the purge-gas supply means 16. The flue gas A discharged from the pipe 9 is flowing in the measurement area (that is, between the incident tube 22 and the emission tube 24). Accordingly, as shown in FIGS. 18A and 18B, a temperature boundary layer 220 generated due to mixing of the purge gas G and the flue gas A is formed at an outlet (one end) of the purge gas G of the incident tube 22. Thus, a fluctuation (noise) is generated in the light reception signal due to the formation of the temperature boundary layer 220. The fluctuation changes according to a relation between the flow velocity of the purge gas G and the flow velocity of the flue gas A.

A relation between the flow velocity and the fluctuation in the light reception signal is calculated in advance by the calculation unit 210 by experiments or the like and stored therein, and the calculation unit 210 calculates the flow velocity based on the light reception signal at the time of measurement. That is, although the calculation result is changed from the flow volume to the flow velocity, the flow velocity is calculated basically in the same method as described above.

In this manner, the flow velocity measurement device allows passage of the laser beam through the measurement area and measures the light reception signal, while supplying purge gas to the incident tube, thereby enabling to calculate the flow velocity. Furthermore, the flow velocity measurement device can perform measurement without providing the main pipe through which flue gas to be measured flows, as in the present embodiment. Therefore, the measurement area can be freely set and thus flexibility of the measurement can be increased. The flow velocity at each position can be measured, for example, by changing the distance between the incident tube and the emission tube to various distances. The distance from a discharge opening of flue gas can be various distances. For example, the flow velocity at an arbitrary position in the pipe can be also measured.

Even when the flow velocity of fluid flowing in an area other than in the pipe is to be detected, the flow of fluid to be measured can be detected more appropriately by detecting the flow of flue gas (the flow in the measurement area) by a flow-direction detection means. Furthermore, as the flow-direction detection means, above-described various methods can be used.

In the case of the flow velocity measurement device, a plurality of relations between the light reception signal and the flow velocity are stored based on other various conditions, and the relation to be used is changed over based on the various conditions, thereby enabling to calculate the flow velocity more accurately.

In the above embodiments, gas in a gaseous form is a measurement object. However, a flow volume and a flow velocity can be measured in a similar manner in a case of liquid. That is, measurement can be performed regardless of gas or liquid, so long as the measurement object is fluid. When the flow volume and the flow velocity of liquid are measured, it is preferred to use liquid as purge fluid.

INDUSTRIAL APPLICABILITY

As described above, the flow volume measurement device and the flow velocity measurement device according to the present invention are useful for measuring a flow volume and a flow velocity of a fluid.

REFERENCE SIGNS LIST 6, 8 pipe
10 flow volume measurement device
12 measurement cell
14 measurement means
16 purge-gas supply means
18 flow-direction detection means
20 main pipe
22 incident tube
24 emission tube
26, 28 window
30, 32 purge-gas supply pipe
40 light emitting unit
42 optical fiber
44 light receiving unit
46 light source driver
48 calculation unit
50 control unit
52 pump
54 drier
56 flowmeter
62, 64 detection element
66 differential pressure detector
200 flow velocity measurement device

The invention claimed is:

1. A flow volume measurement device comprising:
a measurement cell including a main pipe with opposite ends being open and connectable to a flow channel through which fluid flows, an incident tube that is connected to the main pipe and formed with a window for allowing passage of light at an end opposite to a side connected to the main pipe, an emission tube that is connected to the main pipe and formed with a window for allowing passage of light at an end opposite to a side connected to the main pipe, and a first purge-fluid supply tube that is connected to the incident tube;
a purge-fluid supply unit that supplies purge fluid into the first purge-fluid supply tube of the measurement cell;
a light emitting unit that emits a laser beam to the incident tube;
a light receiving unit that receives the laser beam having entered from the incident tube, passed through the measurement cell, and emitted from the emission tube, and outputs a received amount of light as a light reception signal;
a calculation unit that calculates a flow volume of fluid flowing in the measurement cell, based on a light reception signal output from the light receiving unit;
a flow-direction detection unit that detects a flow direction of fluid flowing in the measurement cell;
a control unit that controls an operation of respective units, wherein the purge-fluid has a different temperature or characteristics from the fluid flowing in the measurement cell;
the calculation unit calculates the flow volume of the fluid flowing in the measurement cell based on a relationship between a characteristics change of a light reception signal output from the light receiving unit and the flow volume of the fluid flowing in the measurement cell; and
the calculation unit demodulates a light reception signal received by the light receiving unit by at least one frequency, and calculates the flow volume of the fluid flowing in the measurement cell based on a magnitude of the fluctuation in the demodulated signal in the at least one frequency.

2. The flow volume measurement device according to claim 1, wherein the flow-direction detection unit includes a differential-pressure detection unit that detects a pressure difference in both directions parallel to a flow direction, and detects the flow direction based on the pressure difference detected by the differential-pressure detection unit.

3. The flow volume measurement device according to claim 1, wherein the flow-direction detection unit includes a deforming part that is exposed in the flow channel and deforms due to fluid flow, and detects the flow direction based on a deforming direction of the deforming part.

4. The flow volume measurement device according to claim 1, comprising at least two measurement units including the light emitting unit, the light receiving unit, and the calculation unit, wherein
the flow-direction detection unit detects the flow direction based on calculation values of a flow volume calculated by the measurement units.

5. The flow volume measurement device according to claim 1, wherein
the flow-direction detection unit includes an ultrasonic output unit that outputs an ultrasonic wave to the flow channel and an ultrasonic reception unit that receives the ultrasonic wave output from the ultrasonic output unit, and
detects the flow direction based on a frequency of the ultrasonic wave received by the ultrasonic reception unit.

6. The flow volume measurement device according to claim 1, wherein the calculation unit stores therein a relation between the calculated fluctuation and flow volume in advance, and calculates the flow volume of the fluid based on the relation and the magnitude of the fluctuation.

7. The flow volume measurement device according to claim 1, wherein
the calculation unit stores therein a relation between the calculated fluctuation and the flow volume of the fluid for each flow volume of purge fluid flowing in the incident tube, and
calculates the flow volume of the fluid based on the flow volume of purge fluid flowing in the incident tube and the fluctuation.

8. The flow volume measurement device according to claim 7, wherein the control unit calculates the flow volume of the purge fluid, in which an amount of change in the fluctuation increases in an area including the flow volume of the fluid calculated by the calculation unit, and adjusts the flow volume of the purge fluid to be supplied from the purge-fluid supply unit to the first purge-fluid supply tube based on a calculation result thereof.

9. The flow volume measurement device according to claim 1, wherein the calculation unit also calculates a concentration of a substance to be measured in exhaust fluid flowing in the measurement cell based on an intensity of the laser beam output from the light emitting unit and an intensity of the laser beam received by the light receiving unit.

10. The flow volume measurement device according to claim 1, wherein
the light receiving unit includes a plurality of light receiving elements arranged adjacent to each other, and outputs an amount of light received by each light receiving element as a light reception signal, and
the calculation unit calculates the flow volume of the fluid based on a comparison of intensities of light reception signals transmitted from the respective light receiving elements.

11. The flow volume measurement device according to claim 10, wherein the calculation unit calculates a reached position of the laser beam based on the comparison of intensities of light reception signals transmitted from the respective light receiving elements, and calculates the flow volume of the fluid based on a misalignment between the reached position and a reference position.

12. The flow volume measurement device according to claim 10, wherein the calculation unit also calculates a concentration of a substance to be measured in exhaust fluid flowing in the measurement cell based on a sum total of intensities of light reception signals transmitted from the respective light receiving units and an intensity of the laser beam received by the light receiving unit.

13. The flow volume measurement device according to claim 1, wherein the measurement cell includes a turbulence generation unit that generates turbulence in air flow near the incident tube, in an upstream of the incident tube in a flow direction of the fluid in the main pipe and near the incident tube.

14. The flow volume measurement device according to claim 1, further comprising a second purge-fluid supply tube that is connected to the emission tube, wherein
the purge-fluid supply unit supplies purge fluid also to the second purge-fluid supply tube.

15. The flow volume measurement device according to claim 1, wherein the calculation unit measures a flow velocity of the fluid flowing in the main pipe of the measurement cell based on a light reception signal output from the light receiving unit.

16. The flow volume measurement device according to claim 1, wherein the fluid is a gaseous matter.

17. A flow velocity measurement device comprising:
a measurement cell including an incident tube with one end being an opening facing a measurement area and the other end being formed with a window for allowing passage of light, an emission tube with one end being an opening opposite to the incident tube and facing the measurement area, and the other end being formed with a window for allowing passage of light, and a first purge-fluid supply tube that is connected to the incident tube;
a purge-fluid supply unit that supplies purge fluid into the first purge-fluid supply tube of the measurement cell;
a light emitting unit that emits a laser beam to the incident tube;
a light receiving unit that receives the laser beam having entered from the incident tube, passed through the measurement area, and emitted from the emission tube, and outputs a received amount of light as a light reception signal;
a calculation unit that calculates a flow velocity of fluid flowing in the measurement area, based on a light reception signal output from the light receiving unit;
a flow-direction detection unit that detects a flow direction of fluid flowing in the measurement area;
a control unit that controls an operation of respective units, wherein
the purge-fluid has a different temperature or characteristics from the fluid flowing in the measurement cell;
the calculation unit calculates the flow volume of the fluid flowing in the measurement cell based on a relationship between a characteristics change of a light reception signal output from the light receiving unit, the flow volume of the fluid flowing in the measurement cell, and a diameter of the measurement area; and
the calculation unit demodulates a light reception signal received by the light receiving unit by at least one frequency, and calculates the flow volume of the fluid flowing in the measurement cell based on a magnitude of the fluctuation in the demodulated signal in the at least one frequency.

18. The flow velocity measurement device according to claim 17, wherein the flow-direction detection unit includes a differential-pressure detection unit that detects a pressure difference in both directions parallel to a flow direction, and detects the flow direction based on the pressure difference detected by the differential-pressure detection unit.

19. The flow velocity measurement device according to claim 17, wherein the flow-direction detection unit includes a deforming part that is exposed in the measurement area and deforms due to fluid flow, and detects a flow direction based on a deforming direction of the deforming part.

20. The flow velocity measurement device according to claim 17, wherein
the measurement cell is respectively connected to one end of the incident tube and one end of the emission tube, and has a main pipe through which fluid to be measured flows, and
the measurement area is a part of the main pipe.

21. The flow velocity measurement device according to claim 17, wherein the fluid is a gaseous matter.

* * * * *